(12) United States Patent
Steen et al.

(10) Patent No.: US 9,951,345 B2
(45) Date of Patent: Apr. 24, 2018

(54) HOST CELLS AND METHODS FOR PRODUCING DIACID COMPOUNDS

(71) Applicant: The Regents of the University of California, Oakland, CA (US)

(72) Inventors: Eric J. Steen, San Francisco, CA (US); Jeffrey L. Fortman, San Francisco, CA (US); Jeffrey A. Dietrich, San Francisco, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/900,397

(22) Filed: May 22, 2013

(65) Prior Publication Data

US 2013/0267012 A1 Oct. 10, 2013

Related U.S. Application Data

(63) Continuation of application No. PCT/US2011/061900, filed on Nov. 22, 2011.
(Continued)

(51) Int. Cl.
*C12N 1/20* (2006.01)
*C12N 9/02* (2006.01)
(Continued)

(52) U.S. Cl.
CPC ............ *C12N 15/81* (2013.01); *C12N 1/20* (2013.01); *C12N 9/0077* (2013.01);
(Continued)

(58) Field of Classification Search
None
See application file for complete search history.

(56) References Cited

U.S. PATENT DOCUMENTS 5,254,466 A * 10/1993 Picataggio et al. ............ 435/142
5,620,878 A * 4/1997 Picataggio et al. ............ 435/142
(Continued)

FOREIGN PATENT DOCUMENTS

WO    WO 2007136762 A2 * 11/2007
WO    WO 2009006430 A1 * 1/2009
WO    WO 2013024114 A2 * 2/2013

OTHER PUBLICATIONS

Ost et al., "Rational re-design of the substrate binding site of flavocytochrome P450 BM3". FEBS Letters, vol. 486, pp. 173-177, 2000.*
(Continued)

*Primary Examiner* — Richard C Ekstrom
(74) *Attorney, Agent, or Firm* — Robin C. Chiang; Lawrence Berkeley National Laboratory

(57) ABSTRACT

The present invention provides for a method of producing one or more fatty acid derived dicarboxylic acids in a genetically modified host cell which does not naturally produce the one or more derived fatty acid derived dicarboxylic acids. The invention provides for the biosynthesis of dicarboxylic acid ranging in length from C3 to C26. The host cell can be further modified to increase fatty acid production or export of the desired fatty acid derived compound, and/or decrease fatty acid storage or metabolism.

16 Claims, 4 Drawing Sheets

Related U.S. Application Data

(60) Provisional application No. 61/416,287, filed on Nov. 22, 2010.

(51) Int. Cl.
  *C12P 7/40* (2006.01)
  *C12P 7/46* (2006.01)
  *C12P 7/64* (2006.01)
  *C12N 15/81* (2006.01)

(52) U.S. Cl.
  CPC .............. *C12N 15/815* (2013.01); *C12P 7/40* (2013.01); *C12P 7/46* (2013.01); *C12P 7/6409* (2013.01); *C12Y 114/15003* (2013.01)

(56) References Cited

U.S. PATENT DOCUMENTS

| | | | | |
|---|---|---|---|---|
| 5,648,247 | A * | 7/1997 | Picataggio et al. | 435/142 |
| 6,066,480 | A * | 5/2000 | Mobley et al. | 435/142 |
| 6,503,734 | B1 * | 1/2003 | Craft et al. | 435/69.1 |
| 6,790,640 | B2 * | 9/2004 | Craft et al. | 435/69.1 |
| 7,049,112 | B2 * | 5/2006 | Wilson et al. | 435/189 |
| 7,160,708 | B2 * | 1/2007 | Eirich et al. | 435/189 |
| 7,226,768 | B2 * | 6/2007 | Farinas et al. | 435/189 |
| 7,405,063 | B2 * | 7/2008 | Eirich et al. | 435/123 |
| 8,383,373 | B2 * | 2/2013 | Kamal et al. | 435/132 |
| 2003/0153060 | A1 * | 8/2003 | Wilson et al. | 435/189 |
| 2004/0146999 | A1 * | 7/2004 | Fallon et al. | 435/134 |
| 2004/0265980 | A1 * | 12/2004 | Zhang et al. | 435/134 |
| 2009/0264311 | A1 * | 10/2009 | Arnold et al. | 506/11 |
| 2009/0298143 | A1 * | 12/2009 | Roessler et al. | 435/134 |
| 2010/0154293 | A1 * | 6/2010 | Hom et al. | 44/385 |
| 2010/0196973 | A1 * | 8/2010 | Dubois | 435/135 |
| 2010/0285545 | A1 * | 11/2010 | Gross et al. | 435/134 |
| 2010/0291653 | A1 * | 11/2010 | Ness et al. | 435/171 |
| 2010/0324257 | A1 * | 12/2010 | Karau et al. | 528/310 |
| 2011/0165637 | A1 * | 7/2011 | Pfleger et al. | 435/134 |
| 2012/0077237 | A1 * | 3/2012 | Picataggio et al. | 435/142 |
| 2013/0089899 | A1 * | 4/2013 | Kurek et al. | 435/134 |

OTHER PUBLICATIONS

Imai, "Characterization of rabbit liver cytochrome P-450 (laurate omega-1 hydroxylase) synthesized in transformed yeast cells", Journal of Biochemistry, vol. 103, No. 1, pp. 143-148, 1988.*

Oliver et al., "A single mutation in cytochrome P450 BM3 changes substrate orientation in a catalytic intermediate and the regiospecificity of hydroxylation", Biochemistry, vol. 36, No. 7, pp. 1567-1572, 1997.*

Dehesh et al., "Production of high levels of 8:0 and 10:0 fatty acids in transgenic canola by overexpression of Ch FatB2, a thioesterase cDNA from Cuphea hookeriana", The Plant Journal, vol. 9, No. 2, pp. 167-172, 1996.*

Yuan et al., "Modification of the substrate specificity of an acyl-acyl carrier protein thioesterase by protein engineering", Proceedings of the National Academy of Sciences USA, vol. 92, pp. 10639-10643, 1995.*

Lu et al., "Fatty acid biotransformations: omega-hydroxy- and omega-carboxy fatty acid building blocks using a engineered yeast biocatalyst", Polymer Preprints, vol. 50, No. 2, pp. 29-30, 2009.*

Wheeler, "Analyzing lipid metabolism: activation of beta-oxidation of fatty acids", Methods in Molecular Biology, vol. 465, pp. 47-59, 2009.*

Sandager et al., "Storage lipid synthesis is non-essential in yeast", Journal of Biological Chemistry, vol. 277, No. 8, pp. 6478-6482, 2002.*

Appendix C of U.S. Appl. No. 61/292,918, filed Jan. 7, 2010.*
GenBank Accession No. ABS73418.1, published Sep. 29, 2009.*
GenBank Accession No. BAE02685.1, published Jun. 25, 2005.*
UniProtKB/Swiss-Prot Accession No. P96575.2, published Nov. 3, 2009.*
UniProtKB/Swiss-Prot Accession No. O34893.1, published Nov. 3, 2009.*

* cited by examiner

SEQUENCE LISTING

```
<160> NUMBER OF SEQ ID NOS: 3

<210> SEQ ID NO 1
<211> LENGTH: 14281
<212> TYPE: DNA
<213> ORGANISM: Artificial Sequence
<220> FEATURE:
<223> OTHER INFORMATION: synthetic polyketide synthase (PKS) in
      expression vector

<400> SEQUENCE: 1
gacgtcttaa gacccacttt cacatttaag ttgtttttct aatccgcata tgatcaattc      60
aaggccgaat aagaaggctg gctctgcacc ttggtgatca ataattcga tagcttgtcg     120 taataatggc ggcatactat cagtagtagg tgtttccctt tcttctttag cgacttgatg     180
ctcttgatct tccaatacgc aacctaaagt aaaatgcccc acagcgctga gtgcatataa     240
tgcattctct agtgaaaaac cttgttggca taaaaaggct aattgatttt cgagagtttc     300
atactgtttt tctgtaggcc gtgtacctaa atgtactttt gctccatcgc gatgacttag     360
taaagcacat ctaaaacttt tagcgttatt acgtaaaaaa tcttgccagc tttcccttc     420 taaagggcaa aagtgagtat ggtgcctatc taacatctca atggctaagg cgtcgagcaa     480
agcccgctta ttttttacat gccaatacaa tgtaggctgc tctacaccta gcttctgggc     540
gagtttacgg gttgttaaac cttcgattcc gacctcatta agcagctcta atgcgctgtt     600
aatcacttta cttttatcta atctagacat cattaattcc taattttgt tgacactcta     660
```

```
tcgttgatag agttatttta ccactcccta tcagtgatag agaaaagaat tcaaaagatc    720 tttttaagctc taggaggcat atgcatcatc accatcacca cgcaggtcat ggtgatgcta    780
ctgcacaaaa agctcaagat gcagaaaaat ctgaagacgg ttctgacgct atcgcagtta    840
tcggtatgtc ctgccgtttt cctggcgccc cgggcactgc tgaattttgg cagctgctgt    900
cctctggcgc agatgcagta gtgaccgcag ctgatggccg tcgtcgtggc accatcgacg    960
caccggcgga cttcgacgct gctttcttcg gtatgtcccc tcgcgaagcc gccgccaccg   1020
acccgcaaca gcgcctggtg ctggaactgg gctgggaagc gctggaagat gctggtatcg   1080
ttccggaatc cctgcgtggt gaggctgcct ccgtgttcgt aggcgcgatg aacgatgact   1140
acgcaactct gctgcatcgt gcaggcgctc cgactgacac ttacaccgca actggcctgc   1200
agcacagcat gatcgcgaac cgtctgtcct actttctggg cctgcgcggc ccgtccctgg   1260
tagtagacac cggccagagc agcagcctgg ttgcggtggc cctggcggtt gaatctctgc   1320
gtggtggtac ctctggtatc gccctggccg gtggtgtgaa cctggttctg gcggaagaag   1380
gcagcgcggc tatggaacgt gtaggcgcac tgtccccaga cggtcgctgc catacgtttg   1440
atgcgcgtgc gaacggttat gtacgcgcg aaggcggtgc tattgtcgtt ctgaagccgc   1500
tggccgacgc actggctgac ggcgatcgtg tttactgtgt tgtgcgcggc gtagcgacgg   1560
gcaacgacgg tggcggtccg ggcctgaccg taccagatcg tgcgggtcag gaggcggttc   1620
tgcgtgcagc ttgtgaccaa gcaggtgtac gtccggcgga tgtacgtttc gtggaactgc   1680
atggcactgg caccccctgcc ggcgatccgg ttgaagcaga agctctgggt gcagtctacg   1740
gcactggtcg tccggcgaac gaaccactgc tggtgggctc tgttaagacc aacatcggtc   1800
atctggaggg cgcagctggt atcgcgggct ttgtcaaagc ggctctgtgc ctgcacgagc   1860
gtgcgctgcc ggcgagcctg aacttcgaaa ccccgaaccc ggcgatcccg ctggaacgtc   1920
tgcgcctgaa agttcagact gcgcacgccg ctctgcagcc gggtacgggc ggtgccccgc   1980
tgctggcggg cgtgtccgct ttcggtatgg gcggtaccaa ctgccacgtc gtgctggaag   2040
agactccagg tggtcgtcag ccggccgaaa ccggtcaagc tgatgcgtgt ctgttcagcg   2100
cgagcccgat gctgctgctg agcgcccgtt ctgaacaagc gctgcgtgcg caggctgctc   2160
gtctgcgtga acacctggaa gatagcggcg ctgacccgct ggacatcgcg tactctctgg   2220
cgaccactcg cacccgtttc gaacatcgcg cggctgtacc gtgcggtgac ccggaccgtc   2280
tgagctctgc gctggcagcg ctggcagcgg gtcagacccc gcgtggcgtg cgcatcggtt   2340
ctaccgacgc tgatggtcgc ctggcgctgc tgttcactgg ccagggtgcg cagcatccgg   2400
gtatgggcca agagctgtat accaccgacc cgcacttcgc ggcagctctg acgaagttt   2460 gcgaagaact gcagcgttgc ggtactcaaa acctgcgtga ggtgatgttc actccggatc   2520
aaccggacct gctggaccgt accgaatata cccagccggc cctgtttgct ctgcaaaccg   2580
cgctgtaccg taccctgacc gcgcgtggta cccaggctca tctggtgctg ggtcactccg   2640
ttggcgaaat caccgcagct cacattgcag gcgtcctgga cctgccggac gcagctcgtc   2700
tgatcactgc tcgcgcacat gtaatgggtc agctgcctca tggtggtgca atgctgtctg   2760
ttcaggcagc tgaacacgat ctggatcagc tggcgcatac tcacgcgtg gagatcgcgg   2820 ctgtgaacgg tccgacgcac tgcgttctgt ctggtccgcg taccgcgctg aagaaaccg   2880 cacaacacct gcgcgagcag aacgtgcgtc acacctggct gaaagtttct cacgcgtttc   2940
actccgcact gatggatccg atgctgggtg cgtttcgtga taccctgaac actctgaact   3000
```

```
accagccgcc aactatcccg ctgatttcca acctgaccgg ccagattgct gacccgaatc   3060
acctgtgcac tccggattat tggatcgacc acgcgcgtca cactgtgcgt tttgctgacg   3120
cggttcaaac cgctcatcat caaggcacta ccacttacct ggaaattggt cctcatccga   3180
ctctgaccac cctgctgcat catacccdgg ataaccctac tactattccg acctgcacc   3240 gtgaacgccc ggagccggaa accctgactc aggcaatcgc agctgttggt gtgcgtaccg   3300
acggtatcga ttgggcggtt ctgtgcgcg cgtctcgtcc gcgtcgcgta gaactgccga   3360
cctacgcttt ccagcgtcgt actcattggg cccctggtct gacgccgaac catgcaccgg   3420
ctgaccgtcc ggctgctgaa ccacagcgcg cgatggctgt cggtccggtc agccgtgagg   3480
ccctggtgcg cctggttggt gaaaccaccg cgtccgtgct gggcctggac ggcccagacg   3540
aggtggcgct ggaccgtccg ttcacttctc aaggtctgga ctctatgacc gctgttgaac   3600
tggccggtct gctgggcacc gcggcaggcg ttgctctgga cccaactctg gtttacgaac   3660
tgccgacgcc tcgcgctgtc gcagatcacc tggcaaaaac tctgctgggt gagagcgctg   3720
cggacgcaga tcaggaagtg aacggccgta cgggtgaggc cgaagcgaaa gcgggtgacc   3780
cgatcgctgt aatcggcatc ggttgtcgct cccaggtgg tgtggcgacc ccggacgatc   3840
tgtgggaact ggtagcgtcc ggcaccgatg ctatttccac tttcccaacc gaccgtggct   3900
gggacctgga cggtctgtac gacccggatc cgtctactcc aggtaagtcc tatgttcgcc   3960
atggcggctt tctgcacgat gcggcccagt ttgatgctga attctttggt atctccccgc   4020
gtgaagctac tgcgatggac ccgcaacaac gcctgctgct ggaaactagc tgggaggcac   4080
tggaacgcgc tggcgtagtt ccggagtccc tgcgcggtgg ccgcactggt gttttgtgg   4140 gtactactgc tccggaatat ggcccacgtc tgcacgaagg cactgacggt tatgaaggct   4200
tcctgctgac cggtaccact gcatctgtgg ccagcggtcg tatcgcgtat gccctgggta   4260
cccgtggccc ggcgctgacc gttgacactg cgtgcagcag ctccctggtg gccctgcatc   4320
tggcggtaca atccctgcgt cgtggtgaat gcgacctggc gctggcaggt ggcaccaccg   4380
ttatgtccgg tccgggcatg ttcgttgagt ctcccgcca gcgtggtctg gctcctgacg   4440
gtcgttgcaa gcattctct gcagacgcgg atggcaccgc ctgggccgaa ggtgttggca   4500
tgctgctggt cgaacgtctg tctgacgcgg aacgtctggg tcaccgcgtc ctggcagtcg   4560
tgcgtggcac tgcggtaaat caggacggtg cgtctaacgg tctgacggca ccgtctggcc   4620
ctgcccagca gcaggtgatc cgcgacgcgc tgagcgacgc gggcctgtcc gctgatgaca   4680
ttgatgcggt tgaagctcat ggtaccggca ccgcgctggg tgatccgatc gaagcgggtg   4740
ccctgctggc aacctatggc caccccgaaac gccagacgcc ggtttggctg ggttccctga   4800
aaagcaacat tggccacacg caggcggcgg ctggtattgc tggtatcatc aaaatggttc   4860
aggctctgcg tcacgacacc ctgccgcgta cgctgcacgc cgaccatccg tctagcaaag   4920
tggactggga tgccggccca ctgcagctgc tgaccgacgc tcgtccgtgg ccagcggacc   4980
cggatcgtcc gcgccgtgca ggtatcagcg cttcgcgcgt ctctggtacc aacgcgcacg   5040
ttatcgtaga acagcctgcg ctggtggaat tccagctgc ggaacctagc ggtcgtgaac   5100
caggcgttgt tccgctgcca ctgtctggta aagcccgga agctctgcgt gaccaggcag   5160
ctcgcctgct ggcgggtctg gccgaacgcc cggctctgcg tccgctggat ctgggctatt   5220
ctctggctac cacgcgtagc gcgttcgatc atcgtgcagt agtactggcg acggaccgtg   5280
ccgacgctgt ccgcgcgctg actgctctgg ctgcagcgga tgccgacctg tctgccgtgg   5340
tcggtgatac gcgtactggt cgccacgcgg tcctgttttc cggtcagggt tcccagcgtc   5400
```

-continued

```
tgggcatggg tcgtgagctg tacgaacgct ttcctgtgtt tgctgaagct ctggacgtgg    5460
cgatcgacca cctggatgcc gcactgccgg cgcaagcctc tctgcgcgaa gttatgtggg    5520
gtgatgatgt tgaactgctg gacgaaaccg gttggacgca gccggcgctg ttcgcggtgg    5580
aagtggctct gttccgtctg gttgaaagct ggggcgtccg tccggacttc gttgcgggcc    5640
actctattgg cgaaatcgca gctgcccacg tggttggtgt cttcagcctg aagatgcgt    5700 gccgtctggt agccgcacgt gcgaccctga tgcaggcgct gccgaccggt ggtgctatga    5760
tcgcaattca ggcggctgaa gatgaagtta cccagcatct gactgacgat gtttccatcg    5820
cggccgttaa cggtccgact tctgttgtgg tttctggtgc tgaatctgct gcgcgcaccg    5880
tagcagaccg tctggctgaa aacggccgta aaccactcg cctgcgtgtc tcccacgcat    5940
ttcactctcc gctgatggac ccgatgctgg ccgaattccg tgctgttgct gaaggtctgt    6000
cctatgctac cccgaccctg ccagtagtgt ctaacctgac tggccgtctg gcgactgcag    6060
atgatctgtg ttccgctgaa tactgggccc gtcacgtacg cgaggccgtg cgtttcgcgg    6120
atggcgtttc taccctggaa aatgaaggcg ttaccacctt cctggaactg gtccggacg    6180 gcgtactgag cgcaatggca cagcaatccc tgaccggtga cgccgctacc gttccggcgc    6240
tgcgtaaaga ccgtgatgag gaaacctctg ctctgaccgc gctggcacat ctgcacaccg    6300
cgggtctgcg cgttgactgg gctgcgttct tcgcggggttc cggtgcaact cgcgtggatc    6360
tgccgacgta cgcttttcag cacgcgacct attggccgac cggcacgctg ccgactgccc    6420
acgccgctgc ggttggtctg acggctgctg agcatccgct gctgaatggt agcgttgagc    6480
tggctgaggg cgagggcgta ctgttcactg gtcgcctgtc cctgcaaagc catccatggc    6540
tggcagacca cgcggtcatg ggtcaggttc tgctgcctgg cactgctctg ctggagctgg    6600 cttttccgtgc gggcgacgaa gcgggctgcg accgtgtaga agaactgacc ctggcggctc    6660
cgctggtcct gcctgaacgt ggtgccgttc agacccaggt gcgtgttggc gttgcagacg    6720
acaccggccg tcgcaccgtg accgtacact ctcgcccaga gcatgcgacc gacgtaagct    6780
ggactcagca cgcaaccggt accctgacca tgggttctgc gccggcagac actggtttcg    6840
acgcgaccgc ttggccgccg gcagacgctg aaccgctggc taccgatgat tgctacgcgc    6900
gctttactac cctgggtttc gcgtatggcc cggtgttcca gggcctgcgc gcagcttggc    6960
gtgccggtga tgtcctgtat gccgaagttg ctctggcaga gtccaccggt gatgaagcga    7020
ctgcgtttgg tctgcacccg gccctgctgg acgccgcgct gcacgcgtcc ctggttgcgc    7080
acgaaggtga agagagcaac ggcggcctgc ctttttcttg gaaggtgcc accctgtatg    7140 ctactggcgc aaccgcactg cgcgtgcgcc tgaccccaac cggtaccgat ggccgttccg    7200
ttgcaatcgc ggttgctgat accgcaggcc gtccagtagc ggctatcgac aacctggtgt    7260
cccgccgtgt gagcggtgac cagctgaccg gtgctgcagg tctggctcgt gacgcgctgt    7320
ttactctgga ctgaacccg gttccggaaa acctggttcc agaaaacccg gtcccagaaa    7380
acaccggtgg cggccacgca caagaccagg acggtcgtcc ggctgcggca actgttgcgc    7440
tggtcggcgc ggatggtacg gcaattgctg ctgatctgac cgctgcgggt atccacacta    7500
ccctgcaccc ggacctgacc actctggcca ctacggacgc ggatgtgcct aagaccgttc    7560
tgatcccgct gactggcacc ggcaccggca ctggtacggg tacgagagc actgacggta    7620 tcggtactgg tgctgcggaa tccgatgcgt ctgcgccgag ccctgccgaa gtcgctcaca    7680
ccctgagcac cgcagcgctg cgctggtgc aggaatggac tgcccaagaa cgtttcgccg    7740
```

-continued

```
gcagccgcct ggcgtttgtc accactggcg cgaccgcagc gggtggtact gacgtaatgg    7800
acgtggctgc ggctgcggtc tggggtctgg tacgcagcgc tcagtctgaa gccccggata    7860
cctttgtcct gatcgatcgt gatccgggcc ctgctggcac tcatgaccgc actgcggcag    7920
ccgaacgtgg tcagctgctg ctgcgcgcac tgcacactga cgagccgcag ctggcgctgc    7980
gtgacggtgg cgtgctggct gcgcgtctgg cgcgcttcga taccgctgcc gcgctgaccc    8040
ctccggcgga ccgcgcttgg cgtctggatt ccacggctaa aggtagcctg aacggtctgg    8100
cactgacccc gtatccagcc gcgctggccc cgctgaccgg tcacgaagtt cgtgttgaag    8160
ttcgtgctgc gggcctgaac ttccgcgatg ttctgaacgc cctgggtatg taccctggtg    8220
atgacgtggg ttctttcggt tccgaagcag ctggcgtcgt tgtggaggtg ggcccggagg    8280
ttacgggcct ggccccaggt gatcaggtga tgggcatgat cactggtagc ttcggttctc    8340
tggccgtaga cgacgctcgc cgcctggcgc gtctgccgga agactggagc tgggaaaccg    8400
gcgcttccgt accgctggta ttcctgaccg cgtattacgc cctgaaagaa ctgggtggtc    8460
tgcgtgcagg tgaaaaagta ctggtacacg ctggtgctgg cggtgtgggc atggcggcga    8520
tccagattgc acgtcacgtc ggcgcagaag ttttcgccac cgccagcgaa ggtaaatggg    8580
acgttctgcg ctctctgggt gttgctgatg atcacatcgc ctcctctcgt actctggatt    8640
ttgaagccgc ttttgcagaa gtcgccggtg atcgtggcct ggatgttgtg ctgaactctc    8700
tggccggcga cttcgttgat gcctccatgc gcctgctggg tgacggtggc cgttttctgg    8760
agatgggtaa aactgacatc cgtgcggcag atagcgttcc ggacggtctg tcttaccaat    8820
ccttcgacct ggcttgggtc gtgccggaaa ccattggcac catgctggct gaactgatgg    8880
atctgttccg taccggtgcg ctgcgcccgc tgccggtacg cacgtgggac gtgcgccacg    8940
cgaaagatgc cttccgtttc atgtccatgg ccaaacatat cggtaaaatc gtactgactc    9000
tgccgcgttc ctggaagccg gaaggcaccg tactggtgac cggcggtact ggtggcctgg    9060
gtggcctggt ggcacgtcac ctggttcgca gctgcgcgt ccgtcacctg ctgctgacct    9120
ctcgtagcgg cgttggtgct gcgggtgccg cgggtctggt tgcagaactg gaatctctgg    9180
gcgcacgcgt agttgtcgcg gcgtgtgacg ttggcgacgg tagcgcagtt gcggagctgg    9240
tagctggtgt tagcgaaagc tatcctctgt ctgcagttgt acatgcggcg ggtgttctgg    9300
acgacggtgt tgtaggttcc ctgacccccg aacgcctggc cgctgttctg cgcccgaagg    9360
tcgacggtgc atggaacctg cacgaagcta cccgtggcct ggacctggac gcattcgtgg    9420
tcttctcctc tgtggcaggc gttttttggcg gtgcaggtca ggcgaactac gccgctggta    9480
acgcttttct ggatgccctg atggttcacc gtgtagcggg tggtctgcca ggcgtatctc    9540
tggcttgggg cgcgtgggat caaggcgttg gcatgactgc aggtctgacc gagcgtgacg    9600
tacgccgcgc agcagagtcc ggcatgccgc tgctgactgt tgatcaaggt gtcgctctgt    9660
tcgacgccgc actggcgacg ggcagcgctg ccctggtgcc ggtacgtctg gatctggcgg    9720
ccctgcgtac ccgtggtgac atcgctccgc tgctgcgtgg tctggtaaag gcaccaatcc    9780
gtcgtgccgc tgccaccacc ccgggtgata ccggcctggc agaacagctg acccgtctgc    9840
agcgcgccga acgtcgtgac accctgctgg cactggtgcg cgaccaggca gcgatggtgc    9900
tgggccacac gagcggcgat ggcgtggacc cgtctcgcgc gtttcgtgac ctgggctttg    9960
attctctgac cgctgtggag ctgcgtaacc gtatcggtgc tgctaccggt ctgcgtctgc   10020
cggctaccgc agtattcgat tacccgaccg ctgacgcact ggcagcacac ctgctgaccg   10080
aactggacag cggtacccca gctcgcgaag cgtctagcgc actgcgtgat ggctaccgtc   10140
```

```
aggcaggtgt gtccggccgt gttcgttctt acctggacct gctggcaggt ctgtctgatt    10200
tccgcgaaca cttcgacggt tctgatggtt tctctctgga tctggttgat atggcagatg    10260
gtccgggtga agttactgta atctgttgtg cgggcaccgc tgcgatcagc ggtccacacg    10320
aatttactcg tctggcaggt gctctgcgtg gcattgctcc tgttcgtgcc gttccgcagc    10380
cgggctacga ggagggtgaa ccgctgccgt cctccatggc ggcggtagcc gccgttcagg    10440
ctgatgcggt gatccgtacc caaggcgata aacctttgt cgttgcaggc cacagcgctg     10500
gtgctctgat ggcttacgcc ctggccaccg aactgctgga tcgtggtcac cctccgcgtg    10560
gtgttgtact gatcgatgtt tacccaccgg gtcatcagga cgccatgaac gcatggctgg    10620
aggaactgac cgcgactctg ttcgaccgtg agactgttcg catggatgat acgcgtctga    10680
ctgcactggg cgcatatgac cgcctgactg gtcagtggcg tccgcgtgaa accggtctgc    10740
cgaccctgct ggtgtctgct ggcgaaccga tgggtccgtg gccggacgac tcctggaaac    10800
ctacctggcc ttttgaacat gacactgtgg cagttccggg cgatcacttc actatggttc    10860
aggaacacgc agatgcgatc gcacgtcaca tcgacgcttg gctgggtggc ggtaactctt    10920
aatgagatcc ggctgctaac aaagcccgaa aggaagctga gttggctgct gccaccgctg    10980
agcaataacc ctagggtacg ggttttgctg cccgcaaacg ggctgttctg gtgttgctag    11040
tttgttatca gaatcgcaga tccggcttca gccggtttgc cggctgaaag cgctatttct    11100
tccagaattg ccatgatttt ttccccacgg gaggcgtcac tggctcccgt gttgtcggca    11160
gctttgattc gataagcagc atcgcctgtt tcaggctgtc tatgtgtgac tgttgagctg    11220
taacaagttg tctcaggtgt tcaatttcat gttctagttg ctttgtttta ctggtttcac    11280
ctgttctatt aggtgttaca tgctgttcat ctgttacatt gtcgatctgt tcatggtgaa    11340
cagctttgaa tgcaccaaaa actcgtaaaa gctctgatgt atctatcttt tttacaccgt    11400
tttcatctgt gcatatggac agttttccct tgatatgta acggtgaaca gttgttctac     11460
ttttgtttgt tagtcttgat gcttcactga tagatacaag agccataaga acctcagatc    11520
cttccgtatt tagccagtat gttctctagt gtggttcgtt gttttgcgt gagccatgag     11580 aacgaaccat tgagatcata cttactttgc atgtcactca aaaattttgc ctcaaaactg    11640
gtgagctgaa ttttgcagt taaagcatcg tgtagtgttt ttcttagtcc gttatgtagg     11700
taggaatctg atgtaatggt tgttggtatt ttgtcaccat tcattttat ctggttgttc     11760 tcaagttcgg ttacgagatc catttgtcta tctagttcaa cttggaaaat caacgtatca    11820
gtcgggcggc ctcgcttatc aaccaccaat ttcatattgc tgtaagtgtt taaatcttta    11880
cttattggtt tcaaaaccca ttggttaagc cttttaaact catggtagtt attttcaagc    11940
attaacatga acttaaattc atcaaggcta atctctatat ttgccttgtg agttttcttt    12000
tgtgttagtt cttttaataa ccactcataa atcctcatag agtatttgtt ttcaaaagac    12060
ttaacatgtt ccagattata ttttatgaat ttttttaact ggaaaagata aggcaatatc    12120
tcttcactaa aaactaattc taattttcg cttgagaact tggcatagtt tgtccactgg     12180
aaaatctcaa agcctttaac caaaggattc ctgatttcca cagttctcgt catcagctct    12240
ctggttgctt tagctaatac accataagca ttttccctac tgatgttcat catctgagcg    12300
tattggttat aagtgaacga taccgtccgt tctttccttg tagggttttc aatcgtgggg    12360
ttgagtagtg ccacacagca taaaattagc ttggtttcat gctccgttaa gtcatagcga    12420
ctaatcgcta gttcatttgc tttgaaaaca actaattcag acatacatct caattggtct    12480
```

```
aggtgatttt aatcactata ccaattgaga tgggctagtc aatgataatt actagtcctt    12540
ttcccgggtg atctgggtat ctgtaaattc tgctagacct ttgctggaaa acttgtaaat    12600
tctgctagac cctctgtaaa ttccgctaga cctttgtgtg ttttttttgt ttatattcaa    12660
gtggttataa tttatagaat aaagaaagaa taaaaaaga taaaaagaat agatcccagc     12720
cctgtgtata actcactact ttagtcagtt ccgcagtatt acaaaaggat gtcgcaaacg    12780
ctgtttgctc ctctacaaaa cagaccttaa aaccctaaag cttaagtag caccctcgca     12840 agctcgggca aatcgctgaa tattcctttt gtctccgacc atcaggcacc tgagtcgctg    12900 tcttttcgt gacattcagt tcgctgcgct cacggctctg gcagtgaatg ggggtaaatg     12960
gcactacagg cgccttttat ggattcatgc aaggaaacta cccataatac aagaaaagcc    13020
cgtcacgggc ttctcagggc gttttatggc gggtctgcta tgtggtgcta tctgactttt    13080
tgctgttcag cagttcctgc cctctgattt tccagtctga ccacttcgga ttatcccgtg    13140
acaggtcatt cagactggct aatgcaccca gtaaggcagc ggtatcatca acaggcttac    13200
ccgtcttact gtccctagtg cttggattct caccaataaa aaacgcccgg cggcaaccga    13260
gcgttctgaa caaatccaga tggagttctg aggtcattac tggatctatc aacaggagtc    13320
caagcgagct ctcgaacccc agagtcccgc tcagaagaac tcgtcaagaa ggcgatagaa    13380
ggcgatgcgc tgcgaatcgg gagcggcgat accgtaaagc acgaggaagc ggtcagccca    13440
ttcgccgcca agctcttcag caatatcacg ggtagccaac gctatgtcct gatagcggtc    13500
cgccacaccc agccggccac agtcgatgaa tccagaaaag cggccatttt ccaccatgat    13560
attcggcaag caggcatcgc catgggtcac gacgagatcc tcgccgtcgg catgcgcgc    13620 cttgagcctg gcgaacagtt cggctggcgc gagcccctga tgctcttcgt ccagatcatc    13680
ctgatcgaca agaccggctt ccatccgagt acgtgctcgc tcgatgcgat gtttcgcttg    13740
gtggtcgaat gggcaggtag ccggatcaag cgtatgcagc cgccgcattg catcagccat    13800
gatggatact ttctcggcag gagcaaggtg agatgacagg agatcctgcc ccggcacttc    13860
gcccaatagc agccagtccc ttcccgcttc agtgacaacg tcgagcacag ctgcgcaagg    13920
aacgcccgtc gtggccagcc acgatagccg cgctgcctcg tcctgcagtt cattcagggc    13980
accggacagg tcggtcttga caaaaagaac cgggcgcccc tgcgctgaca gccggaacac    14040
ggcggcatca gagcagccga ttgtctgttg tgcccagtca tagccgaata gcctctccac    14100
ccaagcggcc ggagaacctg cgtgcaatcc atcttgttca atcatgcgaa acgatcctca    14160
tcctgtctct tgatcagatc atgatcccct gcgccatcag atccttggcg caagaaaagc    14220
catccagttt actttgcagg gcttcccaac cttaccagag ggcgccccag ctggcaattc    14280
c                                                                   14281
```

<210> SEQ ID NO 2
<211> LENGTH: 12876
<212> TYPE: DNA
<213> ORGANISM: Artificial Sequence
<220> FEATURE:
<223> OTHER INFORMATION: synthetic polyketide synthase (PKS) in
      expression vector, sequence hex orf 1, pBbA7c_HEX_ORF_1_h

<400> SEQUENCE: 2

```
gacgtcctca ctgcccgctt tccagtcggg aaacctgtcg tgccagctgc attaatgaat      60
cggccaacgc gcggggagag gcggtttgcg tattgggcgc cagggtggtt tttcttttca     120
ccagtgagac gggcaacagc tgattgccct tcaccgcctg gccctgagag agttgcagca    180
```

```
agcggtccac gctggtttgc cccagcaggc gaaaatcctg tttgatggtg gttaacggcg    240
ggatataaca tgagctgtct tcggtatcgt cgtatcccac taccgagatg tccgcaccaa    300
cgcgcagccc ggactcggta atggcgcgca ttgcgcccag cgccatctga tcgttggcaa    360
ccagcatcgc agtgggaacg atgccctcat tcagcatttg catggtttgt tgaaaaccgg    420
acatggcact ccagtcgcct tcccgttccg ctatcggctg aatttgattg cgagtgagat    480
atttatgcca gccagccaga cgcagacgcg ccgagacaga acttaatggg cccgctaaca    540
gcgcgatttg ctggtgaccc aatgcgacca gatgctccac gcccagtcgc gtaccgtctt    600
catgggagaa ataatactg ttgatgggtg tctggtcaga gacatcaaga aataacgccg    660
gaacattagt gcaggcagct tccacagcaa tggcatcctg gtcatccagc ggatagttaa    720
tgatcagccc actgacgcgt tgcgcgagaa gattgtgcac cgccgcttta caggcttcga    780
cgccgcttcg ttctaccatc gacaccacca cgctggcacc cagttgatcg gcgcgagatt    840
taatcgccgc gacaatttgc gacggcgcgt gcagggccag actggaggtg gcaacgccaa    900
tcagcaacga ctgtttgccc gccagttgtt gtgccacgcg gttgggaatg taattcagct    960
ccgccatcgc cgcttccact tttcccgcg ttttcgcaga aacgtggctg gcctggttca    1020
ccacgcggga aacggtctga taagagacac cggcatactc tgcgacatcg tataacgtta    1080
ctggtttcac attcaccacc ctgaattgac tctcttccgg gcgctatcat gccataccgc    1140
gaaaggtttt gcgccattcg atggtgtccg ggatctcgac gctctccctt atgcgactcc    1200
tgcattagga agcagcccag tagtaggttg aggccgttga gcaccgccgc cgcaaggaat    1260
ggtgcatgca aggagatggc gcccaacagt cccccggcca cggggcctgc caccatAccc    1320
acgccgaaac aagcgctcat gagcccgaag tggcgagccc gatcttcccc atcggtgatg    1380
tcggcgatat aggcgccagc aaccgcacct gtggcgccgg tgatgccggc cacgatgcgt    1440
ccggcgtaga ggatcgagat cgatctcgat cccgcgaaat taatacgact cactataggg    1500
gaattgtgag cggataacaa tttcagaatt caaaagatct aggaggcata tgcatcatca    1560
ccatcaccac gcaggtcatg gtgatgctac tgcacaaaaa gctcaagatg cagaaaaatc    1620
tgaagacggt tctgacgcta tcgcagttat cggtatgtcc tgccgttttc ctggcgcccc    1680
gggcactgct gaattctggc agctgctgag ctctggcgca gatgcagtag tgaccgcagc    1740
tgatggccgt cgtcgtggca ccatcgacgc accggcggac ttcgacgctg cttcttcgg    1800 tatgtcccct cgcgaagccg ccgccaccga cccgcaacag cgcctggtgc tggaactggg    1860
ctgggaagcg ctgaagatg ctggtatcgt tccggaatcc ctgcgtggtg aggctgcctc    1920
cgtgttcgta ggcgcgatga acgatgacta cgcaactctg ctgcatcgtg caggcgctcc    1980
gactgacact acaccgcaa ctggcctgca gcacagcatg atcgcgaacc gtctgtccta    2040
cttctctggc ctgcgcggcc cgtccctggt agtagacacc ggccagagca gcagcctggt    2100
tgcggtggcc ctggcggttg aatctctgcg tggtggtacc tctggtatcg ccctggccgg    2160
tggtgtgaac ctggttctgg cggaagaagg cagcgcggct atggaacgtg taggcgcact    2220
gtccccagac ggtcgctgcc atacgtttga tgcgcgtgcg aacggttatg tacgcggcga    2280
aggcggtgca attgtcgttc tgaagccgct ggccgacgca ctggctgacg gcgatcgtgt    2340
ttactgtgtt gtgcgcggcg tagcgacggg caacgacggt ggcggtccgg gcctgaccgt    2400
accagatcgt gcgggtcagg aggcggttct gcgtgcagct tgtgaccaag caggtgtacg    2460
tccggcggat gtacgtttcg tggaactgca tggcactggc acccctgccg gcgatccggt    2520
tgaagcagaa gctctgggtg cagtctacgg cactggtcgt ccggcgaacg aaccactgct    2580
```

```
ggtgggctct gttaagacca acatcggtca tctggagggc gcagctggta tcgcgggctt    2640
tgtcaaagcg gctctgtgcc tgcacgagcg tgcgctgccg gcgagcctga acttcgaaac    2700
cccgaacccg gcgatcccgc tggaacgtct gcgcctgaaa gttcagactg cgcacgccgc    2760
tctgcagccg ggtacgggcg gtggcccgct gctggcgggc gtgtccgctt tcggtatggg    2820
cggtaccaac tgccacgtcg tgctggaaga gactccaggt ggtcgtcagc cggccgaaac    2880
cggtcaagct gatgcgtgtc tgttcagcgc gagcccgatg ctgctgctga cgcccgttc    2940 tgaacaagcg ctgcgtgcgc aggctgctcg tctgcgtgaa cacctggaag atagcggcgc    3000
tgacccgctg gacatcgcgt actctctggc gaccactcgc acccgtttcg aacatcgcgc    3060
ggctgtaccg tgcggtgacc cggaccgtct gagctctgcg ctggcagcgc tggcagcggg    3120
tcagaccccg cgtggcgtgc gcatcggttc taccgacgct gatggtcgcc tggcgctgct    3180
gttcactggc cagggtgcgc agcatccggg tatgggccaa gagctgtata ccaccgaccc    3240
gcacttcgcg gcagctctgg acgaagtttg cgaagaactg cagcgttgcg gtactcaaaa    3300
cctgcgtgag gtgatgttca ctccggatca accggacctg ctggaccgta ccgaatatac    3360
ccagccggcc ctgtttgctc tgcaaaccgc gctgtaccgt accctgaccg cgcgtggtac    3420
ccaggctcat ctggtgctgg gtcactccgt tggcgaaatc accgcagctc acattgcagg    3480
cgtcctggac ctgccggacg cagctcgtct gatcactgct cgcgcacatg taatgggtca    3540
gctgcctcat ggtggtgcaa tgctgtctgt tcaggcagct gaacacgatc tggatcagct    3600
ggcgcatact cacggcgtgg agatcgcggc tgtgaacggt ccgacgcact gcgttctgtc    3660
tggtccgcgt accgcgctgg aagaaaccgc acaacacctg cgcgagcaga acgtgcgtca    3720
cacctggctg aaagtttctc acgcgtttca ctccgcactg atggaccgga tgctgggtgc    3780
gtttcgtgat ccctgaaca ctctgaacta ccagccgcca actatcccgc tgatttccaa    3840
cctgaccggc cagattgctg acccgaatca cctgtgcact ccggattatt ggatcgacca    3900
cgcgcgtcac actgtgcgtt ttgctgacgc ggttcaaacc gctcatcatc aaggcactac    3960
cacttacctg gaaattggtc ctcatccgac tctgaccacc ctgctgcatc ataccctgga    4020
taaccctact actattccga ccctgcaccg tgaacgcccg gagccggaaa ccctgactca    4080
ggcaatcgca gctgttggtg tgcgtaccga cggtatcgat tgggcggttc tgtgcggcgc    4140
gtctcgtccg cgtcgcgtag aactgccgac ctacgctttc agcgtcgta tcattgggc    4200 ccctggtctg acgccgaacc atgcaccggc tgaccgtccg gctgctgaac cacagcgcgc    4260
gatggctgtc ggtccggtca gccgtgaggc cctggtgcgc ctggttggtg aaaccaccgc    4320
gtccgtgctg ggcctggacg gcccagacga ggtggcgctg gaccgtccgt tcacttctca    4380
aggtctggac tctatgaccg ctgttgaact ggccggtctg ctgggcaccg cggcaggcgt    4440
tgctctggac ccaactctgg tttacgaact gccgacgcct cgcgctgtcg cagatcacct    4500
ggcaaaaact ctgctgggtg agagcgctgc ggacgcagat caggaagtga acggccgtac    4560
gggtgaggcc gaagcgaaag cgggtgaccc gatcgctgta atcggcatcg gttgtcgctt    4620
cccaggtggt gtggcgaccc cggacgatct gtgggaactg gtagcgtccg gcaccgatgc    4680
tatttccact ttcccaaccg accgtggctg ggatctggac ggtctgtacg acccggaccc    4740
gtctactcca ggtaagtcct atgttcgcca tggcggcttt ctgcacgatg cggcccagtt    4800
tgatgctgag ttctttggta tctccccgcg tgaagctact gcgatggacc gcaacaacg    4860 cctgctgctg gaaactagct gggaggcact ggaacgcgct ggcgtagttc cggagtccct    4920
```

```
gcgcggtggc cgcactggtg tttttgtggg tactactgct ccggaatatg cccacgtct    4980
gcacgaaggc actgacggtt atgaaggctt cctgctgacc ggtaccactg catctgtggc    5040
cagcggtcgt atcgcgtatg ccctgggtac ccgtggcccg gcgctgaccg ttgacactgc    5100
gtgcagcagc tccctggtgg ccctgcatct ggcggtacaa tccctgcgtc gtggtgaatg    5160
cgacctggcg ctggcaggtg gcaccaccgt tatgtccggt ccgggcatgt tcgttgagtt    5220
ctcccgccag cgtggtctgg ctcctgacgg tcgttgcaag gcattctctg cagacgcgga    5280
tggcaccgcc tgggccgaag gtgttggcat gctgctggtc aacgtctgt ctgacgcgga    5340
acgtctgggt caccgcgtcc tggcagtcgt gcgtggcact gcggtaaatc aggacggtgc    5400
gtctaacggt ctgacggcac cgtctggccc tgcccagcag caggtgatcc gcgacgcgct    5460
gagcgacgcg ggcctgtccg ctgatgacat tgatgcggtt gaagctcatg gtaccggcac    5520
cgcgctgggt gatccgatcg aagcgggtgc cctgctggca acctatggcc acccgaaacg    5580
ccagacgccg gtttggctgg ttccctgaa aagcaacatt ggccacacgc aggcggcggc    5640
tggtattgct ggtatcatca aaatggttca ggctctgcgt cacgacaccc tgccgcgtac    5700
gctgcacgcc gaccatccgt ctagcaaagt ggactgggat ccggcccac tgcagctgct    5760
gaccgacgct cgtccgtggc cagcggaccc ggatcgtccg cgccgtgcag gtatcagcgc    5820
tttcggcgtc tctggcacca acgcgcatgt catcgtggaa gaggcaccgg agtcttctgc    5880
tgacgcggtc gcggaaagcg gtgtgcgtgt cccggttccg gtagttcctt gggtagtttc    5940
tgcgcgtagc gcagaaggtc tggctgctca ggctgaacgc ctggcacgtt cgtgggcga    6000
acgttctgat caggacccgg ttgatatcgg tttctccctg gtgcgctccc gttctctgct    6060
ggaacatcgc gcagttgtgc tgggtaaggg ccgtgatgac ctggtggcag gtctggcgtc    6120
cctggcgtcc gacggtagcg ctactggtgt agtgagcggt gtggcacgtg gtcgcgcacg    6180
cgtggctttc ggcttttctg ccagggtgc acaacgtgtt ggtatgggcg ctgaactggc    6240
ttccgtttac ccagtattcg cagaagctct ggctgaggtg accggcgctc tgggcctgga    6300
cccggaagtt tttggcgacg ttgaccgcct gggccgtacg gaagtaaccc aggctgcgct    6360
gtttgcgttc gaggtcgctg tcgtacgtct gctggaatcc tttggtgtac gcccggatgt    6420
actgattggc cactccatcg gcgaaattgc ggccgcttac gtcgctggcg tgttctctct    6480
gggtgacgca gccgccctgg taggcgcccg tggtcgtctg atgcaagcac tgccggctgg    6540
cggcgttatg gttgcggtac aggccggtga agcggaagtt gttgctgctc tggaaggctt    6600
cgcggatcgt gttagcctgg cggccgttaa cggtccgtcc agcgtcgtgg tttccggtga    6660
ggcagaggcc gtagaacagg ttgttgcacg cctgggtaag gttaaatcca agcgtctgcg    6720
tgtgagccac gcgttccact ccccgctgat ggagccaatg ctggctgact ccgccaggt    6780
cgccgaacaa atcacctaca cgaaccgca gctgccggtt gtgagcaacg tctctggtcg    6840
cctggcagag ccaggcgagc tgacgacgcc agactactgg gtgcgccacg tacgtgaagc    6900
ggttcgtttc ggtgacggtg tacgcgctct ggctgcagat ggtgtgggcg tgctggttga    6960
ggttggcccg gattccgttc tgactgcact ggcacgtgaa agcctggatg gtgaggatgg    7020
cctgcgcgca gttccgctgc tgcgtaaaga tcgcccggag ccgaaaccc tgctgaccgg    7080
tgttgcgcag gcattcactc acggcgttca agtggattgg ccggcactgc tgccgggtgg    7140
tcgccgtgtg gaactgccga cttacgcgtt ccagcgtcgt cgctactggc tggaagatgc    7200
tgaccccgacc ggtggtgacc cggctgccct gggcctgact gcagcagacc cccactgct    7260
gggtgcggcg gtgccgctgg ctgaagacca gggtatcgtt atcacttccc gcctgtctct    7320
```

```
gcgtactcat ccgtggctgg cagaccacga aatcggtggc actgttctgc tgccgggtgc    7380
tggcctggtt gaaatcgcgc tgcgtgcagg cgacgaagta ggctgcggcc gtgtagaaga    7440
actgaccctg gaaattccgc tggttgtgcc gcaggagggt ggtgtaacgg ttcagatccg    7500
tgtaggcgcg cctgatgaaa gcggttggcg tccaatgacc gtacactctc gcactgaccc    7560
tgaggaagaa tggacccgtc acgttagcgg cgtgctgtct ccggacgtgc ctaccgaacg    7620
ttacgacctg ggcgcgtggc cgcctgctgg cgcgaccccg gttgaactgg acggtttcta    7680
cgaagcgtat gctcgtctgg gttacgcgta tggcccgtct tttcagggcc tgcgtgcggc    7740
gtggcgtcgt ggcgatgagg ttttcgcaga agtatctctg ccagttgagg aacaggaaac    7800
cgcgggtcgc ttcaccctgc acccggctct gctggatgcg cactgcaga gcgcgggtgc    7860 aggtgcattc ttcgactccg gcggtagcat cgtctgccg ttcgcctggt ccggtgtttc    7920
tgtgtttgcg gccggtgcgt ctaccgtccg tgtgcgtctg tctccggctg gtccggatgc    7980
ggttactgta gcgctggcgg acccgacggg tgcgccagtg gcgctggttg aacgtctgct    8040
gatcccggaa atgagcccgg agcaactgga acgcgttcgt ggtgaagaaa agaagcgcc    8100 gtatgttctg gactgggttc cggtggaagt tccggctgac gacctggttc gcccggaacg    8160
ctggaccctg ctgggtggtg ctgatgcagg cgtaggcctg gatgttgctg gtgcattcgc    8220
gagcctggag ccatccgacg gcgctccgga atttgttgtt ctgccgtgtg tgccgccgac    8280
tagcccaacc cgcgctgcgg acgttcgcca gtctaccctg caggcgctga ctgtcctgca    8340
aaattgggtg accgacgagc gccatgccga tagccgcctg gtgctggtta cccgtcgcgc    8400
ggttggcgtg ggtgcccacg acgatgttcc ggacctgacc catgcggctc tgtgggcct    8460 ggtgcgtagc gcgcagaccg aaaacccagg ccgtttcctg ctggtagacc tggatgaagg    8520
tgcggaactg gccgaggttc tgccaggtgc tctgggtagc ggcgaatctc aggttgctgt    8580
acgtgctggt cgtgtgctgg cggctcgtct ggcccgtagc ggtagcggtg gcgcagaact    8640
ggtgccgcct gcaggcgcac cgtggcgtct ggatactacc tctccgggta ccctggagaa    8700
cctggcgctg gtaccgagcg cagaagagcc tctgggtccg ctggacgttc gtgtttccgt    8760
gcgtgcggct ggcctgaact ttcgcgatgt tctgatcgcg ctgggcatgt acccaggtga    8820
cgctcgcatg ggtggcgaag gtgccggcgt tgtaaccgat gtaggttctg aagtaactac    8880
cctggcaccg ggtgaccgtg taatgggtat gctgtcttct gccttcggcc cgaccgccgt    8940
atctgatcat cgtgcgctgg ttcgcgttcc agacgactgg tcttttgaac aggctgcttc    9000
cgttccaacg gttttcgcaa ccgcatacta tggcctggtc gacctggccg agctgcgtgc    9060
gggccagtct gttctggttc acgccgctgc gggtggcgtt ggtatggctg cagtgcagct    9120
ggctcgccat ctgggtgccg aagttttttgg tactgcgagc accggcaaat gggactctct    9180
gcgcgcaggt ggtctggatg ccgaacacat cgcgtccagc cgcaccgttg aatttgaaga    9240
aaccttcctg gcagccaccg ctggccgtgg tgttgatgtg gtcctggatt ccctggcggg    9300
cgagttcgta gacgcctctc tgcgcctgct gccgcgtggc ggtcgttttg tcgagatggg    9360
caaagcagat attcgtgatg cagagcgcgt cgcagctgat catccgggtg tgacctaccg    9420
ttccttcgat ctgctggaag cgggtctgga tcgcttccaa gaaatcctga ctgaagttgt    9480
gcgtctgttc gaacgtggcg tactgcgtca cctgccggtg acggcgtggg atgttcgtcg    9540
tgccgcagaa gcgttccgtt tcgttagcca ggcccgtcac gttggcaaaa acgtactggt    9600
tatgccgcgt gtttgggatc gtgacggtac ggtgctgatc actggcggta ccggtgcgct    9660
```

```
gggcgctctg gttgcacgcc atctggttgc agaacacggc atgcgcaacg tgctgctggc    9720
cggtcgtcgt ggcgttgacg ctccgggtgc ccgtgagctg ctggcagaac tggaaaccgc    9780
cggtgcccag gtaagcgtag ttgcatgtga cgtggctgac cgcgatgctg tggccgagct    9840
gattgcaaag gtgccggtag aacatccact gaccgcagtc gttcataccg ccggtgtagt    9900
cgccgacgct acgctgactg ccctggacgc cgaacgtgtt gataccgtac tgcgtgccaa    9960
ggttgacgcg gtgctgcacc tgcacgaagc gacgcgtggc ctggacctgg cgggtttcgt   10020
cctgttctcc tctgcatctg gtatctttgg cagccctggt cagggtaact acgcggcagc   10080
aaactccttt atcgacgcgt ttgcacatca tcgtcgtgcg cagggtctgc cagcactgtc   10140
tctggcttgg ggcctgtggg cgcgcacgtc tggcatggcc ggtcagctgg ccacgacga    10200 cgttgctcgc atctcccgta ctggtctggc gccgattacc gacgatcagg gtatggcgct   10260
gctggacgct gcgctgggtg ctggtcgtcc actgctggtt cctgtgcgtc tggatcgtgc   10320
ggcgctgcgt agccaggcaa ccgcaggtac cctgccgccg atcctgcgtg gtctggttcg   10380
tgcgaccgtt cgtcgtgctg ctagcactgc ggctgcccaa ggtccatctc tggctgaacg   10440
tctggcgggt ctgccggtaa ccgaacacga acgcattgtg gttgagctgg tgcgcgcgga   10500
tctggcggct gttctgggcc acagcagctc cgctggtatc gatccgggcc gtgcgttcca   10560
agacatgggc attgactccc tgaccgcagt tgagctgcgt aaccgcctga acggtgcaac   10620
gggtctgcgt ctggcggcaa gcctggtttt cgattatccg accccgaacg cgctggcaac   10680
ccacatcctg gacgaactgg cgctggacac tgctggcgcg ggtgctgcag gtgaaccgga   10740
tggtcctgct ccagcaccgg cggacgaagc ccgcttccgt cgtgtaatta actccatccc   10800
tctggatcgc attcgccgtg cgggtctgct ggacgcgctg ctgggtctgg cgggtacctc   10860
tgcagatacc gcagcgtccg acgattttga tcaggaagaa gacggtccgg ccatcgcgag   10920
catggatgta gacgatctgg ttcgtatcgc gctgggtgaa tctgacacca ccgcggacat   10980
cactgagggc actgatcgca gctgataagg atccaaactc gagtaaggat ctccaggcat   11040
caaataaaac gaaaggctca gtcgaaagac tgggcctttc gttttatctg ttgtttgtcg   11100
gtgaacgctc tctactagag tcacactggc tcaccttcgg gtgggccttt ctgcgtttat   11160
acctagggat atattccgct tcctcgctca ctgactcgct acgctcggtc gttcgactgc   11220
ggcgagcgga atggcttacg aacggggcg gagatttcct ggaagatgcc aggaagatac   11280
ttaacaggga agtgagaggg ccgcggcaaa gccgttttc cataggctcc gcccccctga   11340
caagcatcac gaaatctgac gctcaaatca gtggtggcga aacccgacag gactataaag   11400
ataccaggcg tttccccctg gcggctccct cgtgcgctct cctgttcctg cctttcggtt   11460
taccggtgtc attccgctgt tatggccgcg tttgtctcat tccacgcctg acactcagtt   11520
ccgggtaggc agttcgctcc aagctggact gtatgcacga accccccgtt cagtccgacc   11580
gctgcgcctt atccggtaac tatcgtcttg agtccaaccc ggaaagacat gcaaagcac    11640 cactggcagc agccactggt aattgattta gaggagttag tcttgaagtc atgcgccggt   11700
taaggctaaa ctgaaaggac aagttttggt gactgcgctc ctccaagcca gttacctcgg   11760
ttcaaagagt tggtagctca gagaaccttc gaaaaaccgc cctgcaaggc ggttttttcg   11820
ttttcagagc aagagattac gcgcagacca aaacgatctc aagaagatca tcttattaat   11880
cagataaaat atttctagat ttcagtgcaa tttatctctt caaatgtagc acctgaagtc   11940
agccccatac gatataagtt gttactagtg cttggattct caccaataaa aaacgcccgg   12000
cggcaaccga gcgttctgaa caaatccaga tggagttctg aggtcattac tggatctatc   12060
```

```
aacaggagtc caagcgagct cgatatcaaa ttacgcccg ccctgccact catcgcagta    12120
ctgttgtaat tcattaagca ttctgccgac atggaagcca tcacaaacgg catgatgaac    12180
ctgaatcgcc agcggcatca gcaccttgtc gccttgcgta taatatttgc ccatggtgaa    12240
aacgggggcg aagaagttgt ccatattggc cacgtttaaa tcaaaactgg tgaaactcac    12300
ccagggattg gctgagacga aaaacatatt ctcaataaac cctttaggga ataggccag     12360 gttttcaccg taacacgcca catcttgcga atatatgtgt agaaactgcc ggaaatcgtc    12420
gtggtattca ctccagagcg atgaaaacgt tcagtttgc tcatggaaaa cggtgtaaca    12480
agggtgaaca ctatcccata tcaccagctc accgtctttc attgccatac gaaattccgg    12540
atgagcattc atcaggcggg caagaatgtg aataaaggcc ggataaaact tgtgcttatt    12600
tttctttacg gtctttaaaa aggccgtaat atccagctga acgtctggt tataggtaca     12660 ttgagcaact gactgaaatg cctcaaaatg ttctttacga tgccattggg atatatcaac    12720
ggtggtatat ccagtgattt ttttctccat tttagcttcc ttagctcctg aaaatctcga    12780
taactcaaaa aatacgcccg gtagtgatct tatttcatta tggtgaaagt tggaacctct    12840
tacgtgccga tcaacgtctc attttcgcca gatatc                             12876
```

<210> SEQ ID NO 3
<211> LENGTH: 10560
<212> TYPE: DNA
<213> ORGANISM: Artificial Sequence
<220> FEATURE:
<223> OTHER INFORMATION: synthetic polyketide synthase (PKS) in expression vector, sequence hex orf 2

<400> SEQUENCE: 3

```
gacgtcctca ctgcccgctt tccagtcggg aaacctgtcg tgccagctgc attaatgaat      60
cggccaacgc gcggggagag gcggtttgcg tattgggcgc cagggtggtt tttcttttca     120
ccagtgagac gggcaacagc tgattgccct tcaccgcctg gccctgagag agttgcagca     180
agcggtccac gctggtttgc cccagcaggc gaaaatcctg tttgatggtg gttaacggcg     240
ggatataaca tgagctgtct tcggtatcgt cgtatcccac taccgagatg tccgcaccaa     300
cgcgcagccc ggactcggta atggcgcgca ttgcgcccag cgccatctga tcgttggcaa     360
ccagcatcgc agtgggaacg atgccctcat tcagcatttg catggtttgt tgaaaaccgg     420
acatggcact ccagtcgcct tcccgttccg ctatcggctg aatttgattg cgagtgagat     480
atttatgcca gccagccaga cgcagacgcg ccgagacaga acttaatggg cccgctaaca     540
gcgcgatttg ctggtgaccc aatgcgacca gatgctccac gcccagtcgc gtaccgtctt     600
catgggagaa ataatactg ttgatgggtg tctggtcaga gacatcaaga ataacgccg       660 gaacattagt gcaggcagct tccacagcaa tggcatcctg gtcatccagc ggatagttaa     720
tgatcagccc actgacgcgt tgcgcgagaa gattgtgcac cgccgcttta caggcttcga    780
cgccgcttcg ttctaccatc gacaccacca cgctggcacc cagttgatcg cgcgagatt      840 taatcgccgc gacaatttgc gacggcgcgt gcagggccag actggaggtg caacgccaa      900 tcagcaacga ctgtttgccc gccagttgtt gtgccacgcg gttgggaatg taattcagct     960
ccgccatcgc cgcttccact ttttcccgcg ttttcgcaga aacgtggctg gcctggttca    1020
ccacgcggga aacggtctga taagagacac cggcatactc tgcgacatcg tataacgtta    1080
ctggtttcac attcaccacc ctgaattgac tctcttccgg cgctatcat gccataccgc     1140 gaaaggtttt gcgccattcg atggtgtccg ggatctcgac gctctcccct tatgcgactcc   1200
```

```
tgcattagga agcagcccag tagtaggttg aggccgttga gcaccgccgc cgcaaggaat    1260
ggtgcatgca aggagatggc gcccaacagt cccccggcca cggggcctgc caccataccc    1320
acgccgaaac aagcgctcat gagcccgaag tggcgagccc gatcttcccc atcggtgatg    1380
tcggcgatat aggcgccagc aaccgcacct gtggcgccgg tgatgccggc cacgatgcgt    1440
ccggcgtaga ggatcgagat cgatctcgat cccgcgaaat taatacgact cactataggg    1500
gaattgtgag cggataacaa tttcagaatt caaaagatct aggaggcata tgtcttccgc    1560
atccagcgag aaaattgttg aggcactgcg cgcaagcctg actgagaacg aacgtctgcg    1620
tcgcctgaac caggaactgg cggctgcggc ccatgaaccg gtagcgatcg tgtctatggc    1680
gtgccgcttc ccaggcggcg ttgaaagccc ggaagatttc tgggacctga tttctgaagg    1740
ccgtgacgca gtatctggtc tgccggataa ccgtggctgg gatctggatg cactgtacga    1800
ccctgacccg gaagcacagg gcaaaaccta cgttcgcgaa ggcgcttttc tgtatgatgc    1860
agccgagttc gacgccgaac tgtttggcat ctccccgcgt gaagctctgg cgatggaccc    1920
gcagcagcgt ctgctgatgg aaaccagctg ggaagttctg gaacgtgcgg gcattcgtcc    1980
agactctctg cgcggcaaac ctgtgggcgt gttcaccggt ggcatcacca gcgactacgt    2040
cacccgccac tatgcatctg gcaccgctcc gcagctgccg tccggtgttg aaagccattt    2100
catgactggt tctgcaggtt ccgtcttctc tggccgtatc gcctatacct acggtttcga    2160
aggtccggca gttactgtcg atactgcgtg ttcttcttct ctggttgctc tgcacatggc    2220
tgcacagagc ctgcgtcagg gcgagtgttc cctggcgttc gccggtggcg ttgcggtcct    2280
gccaaacccg ggtactttcg ttggcttctc ccgtcaacgc gcgctgagcc agacggtcg    2340 ttgcaaagct ttcagcgcag atgcagatgg taccggttgg ggcgagggcg ctggtctggt    2400
tctgctggag aaactgtctg acgctcgtcg taacggtcac ccggtactgg caattctgcg    2460
tggcagcgct gtgaaccaag atggcgcaag caatggcctg actgcaccta acggccgtc    2520 tcagcagcgc gtcattcgtg ccgcgctggc gaacgctcgc ctgagcccgg atgatgtcga    2580
tgtggttgaa gcccacggca ccggtactcc gctgggtgac cctattgagg cgcaggcact    2640
gcaggctact tatggccgtt cccgcagcgc ggaacgtccg ctgtggctgg ttctgtgaa    2700 atctaacgtt gctcatgcac aggcagctgc tggcgttgca agcgtcatca agttgtgat    2760 ggctctgcgc caccgtctgc tgccgaagac gctgcatgct gacgaacgtt ctccgcacat    2820
cgactggcac tccggtgcgg ttgaactgct gaccgaagca cgcgagtggt cccgtaccga    2880
aggccgtgct cgtcgcgcag gcgtttcttc ctttggtatc tctggcacta acgcccacgt    2940
ggtcattgtc gaacaggcac cggacacgcc tgcggaagca gccgacgata tcccgccgcg    3000
tacgccacgc actctgccgt ggctgctgtc tgcgcgcacc ggtgctgctc tgcgtgacca    3060
ggcaaccgcc ctgctggacc atctggatcg tccggacggt gatcgcggtc ctactgctct    3120
ggataccgct ttctctctgg ctaccacccg cgcggccctg aacaccgtc tggctgtggt    3180 gaccggtact gatggcactg ccggtcgcga cgccctgacc gcgtggctgg cccatggtac    3240
tgcaccggac gcgcacgaag gtcacgcggc gggtcgcact cgttgtgcag ctctgttcag    3300
cggtcaaggt gcgcaacgtc tgggcatggg ccgcgaactg cacgcacgtt tcccagtatt    3360
cgcacgcgct ctggatacc cggttgacct gctggatgca gaactgggcg gtaccctgcg    3420
cgaagtgatt tggggcactg acgatgcgcc gctgaacgaa accggttta tcagccggc    3480 actgttcgcg gttgaggttg cactgtatcg cctgattgaa tcctggggtg ttgcaccgga    3540
```

```
tttcgtggca ggccactcta ttggcgaaat cgcggctgcg cacgttgccg gcgtgttctc    3600
cctggaggac gcatgtactc tggtggctgc tcgtgctggc ctgatgcagg cactgccgcg    3660
tggtggtgct atggtggccg tagaagccac tgaagacgaa gtatcccgc tgctgactga    3720
cggcgttgcc attgcggcga tcaacggccc gacttctctg gttgtttccg gcgacgagac    3780
cgcgaccctg gcggtggcag cgcgtctggc ggaacagggt cgtcgtacca cgcgcctgcg    3840
cgttagccac gccttccaca gcccgctgat ggacccgatg ctggctgaat tcgcgctgt    3900
agcggaaggt ctgtcctacg gcgagccgca gatcccagtg gtgtccaacc tgaccggtgc    3960
agtagctgat ggcacgctgc tgggtacggc ggactactgg gtgcgtcacg ttcgtgaagc    4020
agtacgcttc gcagacggca ttcgcgcact gactgatgct ggtgtcggcg cattcctgga    4080
actgggtcca gacggtaccc tggcagcgct ggcacagcaa agcgcaccgg atgcggtaag    4140
cgtaccggtt ctgcgcaaag accgcgacga agaaccggcg gcagttgcgg cactggctcg    4200
tctgcacacc gcgggcgtgc cggttgactg gaccgctttt tacgctggca ccggtgctca    4260
ccgtacggat ctgcctacct acgcgtttca gtatgagcgc tactgccaa aagctactta    4320
ccgtccggcg gacgctaccg gtctgggtct gaccgcagct gaccaccgc tgctgggtgc    4380
ggctatgtct gtgcgggtt ccgacgaact gctgctgact ggtactctgt ctctggctac    4440
ccacccatgg ctggcggacc atgtcgtagg cggtatggtg ttcttcccgg gcaccggctt    4500
cctggagctg gcggtacgtg cagccgacca ggtgggctgt gatcgcgtag aagaactgat    4560
gctggccgca ccgctgattc tgccggcgac cggcactgtg cagatgcaga tcgccgttgg    4620
cgctgcagat gacgatggtg gccgtgatct gcgcttcttc acccgtccgg gcgacgatcc    4680
ggacgctgct tgggcgcagc atgcgacggg ccgtatcacc gaaggcgaac gcgtgctggc    4740
tctggatacc actacctggc cgcctcgtga cgcagaaccg gttgacatcg acggtctgta    4800
cgatcgttac cgtgctaacg gtctggatta cggcccggtg ttccgcggcc tgcgtgcggt    4860
ttggcgtcgt gacaccgaga tttatgcaga agtagcactg cctgaaggca cggcggatgc    4920
cgatgcattc ggtctgcacc cggccctgtt tgacgccgta ctgcactcta ccctgtttgc    4980
gagcgcagac ggtgatgatc gttctctgct gccttttgcc tggaacggcg tcagcctgca    5040
cgccgctggc gctgacgcac tgcgtgttcg tattacgtct tgcggtccgg atgctgttga    5100
aatcacggct gttgacccac agggtcgccc ggttgtgtcc gttgagtctc tgaccctgcg    5160
tgctgctggt ccagatgcag gcaccgctga ccaccgtgca gacgccggca gcctgtttcg    5220
tatggattgg acgccgcgca ctgtacacgc accggctacc ccggcgacct gggccgtact    5280
gggcactgac ccgatcggtc tgaccgaagc actgaccgct gcaggtccgg acacggtaac    5340
tggtctgcgc gacggcgtcg atgctctggg tgaactgacc gcaggcgacg atcgtccagt    5400
gccggatgtg gtagcggttc cactgcgcgg cgcgaccgac cacggtcctg ccggtgcgca    5460
cgacctgacc cgcacggttc tggccctgct gcaggaatgg ctggctgaag aacgtttcgc    5520
gcgctctcgc ctgctgctgg ttacccgcgg tgcggtggca gatggtgaac gtggcccgct    5580
ggacctggcg gctgcaccgg tgtggggtct ggtccgttcc gctcagtctg aaaacccggg    5640
tcgcctgctg ctggttgatc tggacgacac tgccgaatct gcggcgcaac tgccgctgct    5700
gcctgcgctg ctggacgctg acgaaccaca ggcggttgtc cgtgagggca ccgttcgtgt    5760
aggccgtctg gcacgtctgg actccggtcg tggtctggtc ccacctccag gtactccgtg    5820
gcgtctgggt tcccgtgcca agggttccct ggacggtctg gcgctgctgc cgcacccgta    5880
agcgcgtcgc cctctgaccg gccatgaagt tcgtgtaggc atccgcgctg caggtctgaa    5940
```

```
cttccgtgat gtcctgaacg ccctgggtat gtacccgggc gacgccggcc tgtttggcag    6000
cgaggcggca ggtgttgttg tggaagtagg tccggaggtt acgggtctgg ctccgggtga    6060
ccgtgtgatg ggcatgctgt tcggcggctt tggccctctg ggcatcgccg atgcgcgtct    6120
gctgactcca gttccggcag actggtcctg ggaaacgggt gcatctgtcc ctctggtttt    6180
tctgacggcg tactatgccc tgaaagaact gggcggtctg cgtgcaggtg aaaaagtact    6240
ggtccacgcc ggtgccggtg gtgtaggcat ggcggctatc cagatcgcgc gtcacgttgg    6300
tgcggaagtt ttcgcaactg caagcgaagg caagtgggat gtgctgcgtt ctctgggcgt    6360
tgctgacgac cacattgctt cctcccgtac tctggacttc gaagcagctt cgctgaagt    6420 tgcgggtgac cgtggcctgg atgttgttct gaatgctctg tctggtgagt tgtggacgc    6480 ctccatgcgt ctgctgggtg atggcggtcg ttttctggag atgggcaaaa cggacatccg    6540
tgcggcagac tctgtgccgg acggcctgag ctaccacagc ttcgacctgg gtatggttga    6600
tccggaacac atccagcgca tgctgctgga cctggtggaa ctgttcgacc gtggtgcgct    6660
ggcagccctg ccagttcgct cttgggatgt tcgtcgtgct ggcgaggcgt ttcgtttcat    6720
gtccctggcg cagcacattg gtaagattgt tctgactgtt ccgcagccgc tggacccgga    6780
cggtactgtg ctgctgaccg gcggcactgg cggtctggca ggtctgctgg cacgccacct    6840
ggtaaccgag catggtgctc gtcatctgct gctggctggt cgccgtgcc cggatgcgcc    6900 aggcgctgct gcactgcacg cggaactgac tgccctgggc gcggaggtaa ccgttgctgc    6960
ttgtgatgtt gctgaccgta ccgcgctggc ggcgctgctg gctactgtgc cggcagaaca    7020
tcctctgacc gcagttgtgc acactgctgg cgtcctggac gatggcaccc tgaccgcact    7080
gaacccggat cgtctggcga ccgttctgcg cccgaaagtg gacgccgctt ggcacctgca    7140
cgacctgacc cgtcacctgg atctggcagc gttcgttctg tattcctcta ctgcaggcgt    7200
catgggtggt ccgggtcagg ctaactacgc cgctggcaac accttcctgg atgctctggc    7260
agcacaccgt cacgccctgg gtctgccggc tacctccctg gcgtggggtg cttgggaaca    7320
gggcgctggt atgaccggcg ctctgaccga tcatgatctg cgtcgtgtgt ccgacgcggg    7380
tggtcagccg ctgctgactg cagaacgtgg tctggcgctg tacgatgcgg ccactgcagc    7440
agacgaacct ctgatcgtgc cgctgggtct gaccggcggt gctctgcctg ctggcgttgg    7500
cgtgccagcc gtactgcgcg gcctggtacg tactgcgggc cgtcgtgcgc gtgctggtac    7560
cgccggtgtc tcccgtgccg gcctggccga acgtctggca gcactgccgg aggaggaacg    7620
tactcctttt ctggttgaac tggtacgtac cgaagcagca accgtcctgg ccacggtag    7680 cactgacccg gttgacgcac gccgtgaatt tcgtcagctg ggcttcgact ccctgactgc    7740
tattgagctg cgtaatcgcc tgggcaaagc tacgggtctg accctgccag ccaccctgat    7800
ctttgattat ccgaccgtgc gtcgtctggc tgaccatatt ggtcagcagc tggactctgg    7860
taccccagcc cgcgaagcct cctctgctct gcgtgatggt tatcgtcagg ctggtgttag    7920
cggtcgcgtc cgttcttatc tggacctgct ggcgggcctg tctgactttc gtgaacactt    7980
tgatggtagc gatggtttct ccctggacct ggttgacatg gcggacggtc cgggtgaagt    8040
tactgtcatc tgctgtgccg gcactgcagc tatctctggc ccgcatgaat tactcgcct    8100 ggcaggcgca ctgcgtggta tcgcaccggt ccgtgctgtt ccgcagccgg gctacgaaga    8160
aggtgagccg ctgcctagca gcatggctgc agttgcggca gttcaggcag acgccgttat    8220
ccgcacccag ggcgacaagc cgttcgtggt cgctggtcac tccgcaggtg cgctgatggc    8280
```

```
ttatgcactg gcgactgaac tgctggatcg tggtcatcca ccgcgtggtg ttgtactgat    8340
cgacgtgtac ccgccgggtc atcaggacgc tatgaatgct tggctggagg agctgacggc    8400
cactctgttc gaccgtgaga ctgtgcgtat ggatgacacc cgcctgaccg ctctgggcgc    8460
atacgaccgt ctgactggcc agtggcgtcc acgcgagact ggcctgccga ctctgctggt    8520
atctgcaggt gaacctatgg gcccgtggcc ggacgactct tggaagccga cctggccttt    8580
cgaacacgac accgttgcag taccgggcga ccactttact atggtccagg aacatgcgga    8640
cgctattgct cgtcacattg atgcttggct gggcggtggt aatagctgat aaggatccaa    8700
actcgagtaa ggatctccag gcatcaaata aaacgaaagg ctcagtcgaa agactgggcc    8760
tttcgtttta tctgttgttt gtcggtgaac gctctctact agagtcacac tggctcacct    8820
tcgggtgggc ctttctgcgt ttataccta g gatatattc cgcttcctcg ctcactgact    8880
cgctacgctc ggtcgttcga ctgcggcgag cggaaatggc ttacgaacgg gcggagatt    8940
tcctggaaga tgccaggaag atacttaaca gggaagtgag agggccgcgg caaagccgtt    9000
tttccatagg ctccgccccc ctgacaagca tcacgaaatc tgacgctcaa atcagtggtg    9060
gcgaaacccg acaggactat aaagatacca ggcgtttccc cctggcggct ccctcgtgcg    9120
ctctcctgtt cctgcctttc ggtttaccgg tgtcattccg ctgttatggc cgcgtttgtc    9180
tcattccacg cctgacactc agttccgggt aggcagttcg ctccaagctg gactgtatgc    9240
acgaaccccc cgttcagtcc gaccgctgcg ccttatccgg taactatcgt cttgagtcca    9300
acccggaaag acatgcaaaa gcaccactgg cagcagccac tggtaattga tttagaggag    9360
ttagtcttga agtcatgcgc cggttaaggc taaactgaaa ggacaagttt tggtgactgc    9420
gctcctccaa gccagttacc tcggttcaaa gagttggtag ctcagagaac cttcgaaaaa    9480
ccgccctgca aggcggtttt ttcgttttca gagcaagaga ttacgcgcag accaaaacga    9540
tctcaagaag atcatcttat taatcagata aaatatttct agatttcagt gcaatttatc    9600
tcttcaaatg tagcacctga agtcagcccc atacgatata agttgttact agtgcttgga    9660
ttctcaccaa taaaaaacgc ccggcggcaa ccgagcgttc tgaacaaatc cagatggagt    9720
tctgaggtca ttactggatc tatcaacagg agtccaagcg agctcgatat caaattacgc    9780
cccgccctgc cactcatcgc agtactgttg taattcatta agcattctgc cgacatggaa    9840
gccatcacaa acggcatgat gaacctgaat cgccagcggc atcagcacct tgtcgccttg    9900
cgtataatat ttgcccatgg tgaaaacggg ggcgaagaag ttgtccatat tggccacgtt    9960
taaatcaaaa ctggtgaaac tcacccaggg attggctgag acgaaaaaca tattctcaat   10020
aaacccttta gggaaatagg ccaggttttc accgtaacac gccacatctt gcgaatatat   10080
gtgtagaaac tgccggaaat cgtcgtggta ttcactccag agcgatgaaa acgtttcagt   10140
ttgctcatgg aaaacggtgt aacaagggtg aacactatcc catatcacca gctcaccgtc   10200
tttcattgcc atacgaaatt ccggatgagc attcatcagg cggcaagaa tgtgaataaa   10260
ggccggataa aacttgtgct tattttctt tacggtcttt aaaaaggccg taatatccag   10320
ctgaacggtc tggttatagg tacattgagc aactgactga aatgcctcaa atgttcttt   10380
acgatgccat tgggatatat caacggtggt atatccagtg atttttttct ccatttttagc   10440
ttccttagct cctgaaaatc tcgataactc aaaaaatacg cccggtagtg atcttatttc   10500
attatggtga aagttggaac ctcttacgtg ccgatcaacg tctcattttc gccagatatc   10560
```

HOST CELLS AND METHODS FOR PRODUCING DIACID COMPOUNDS

CROSS-REFERENCE TO RELATED APPLICATIONS

This application claims benefit of priority as a continuation application to PCT International Patent Application No. PCT/US2011/061900, filed Nov. 22, 2011, which claims priority to U.S. Provisional Patent Application Ser. No. 61/416,287, filed Nov. 22, 2010, both of which are herein incorporated by reference.

STATEMENT AS TO RIGHTS TO INVENTIONS MADE UNDER FEDERALLY SPONSORED RESEARCH AND DEVELOPMENT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of production of dicarboxylic acids or diacid compounds derived from fatty acids, and in particular, host cells that are genetically modified to produce fatty acid-derived diacids.

BACKGROUND OF THE INVENTION

Aliphatic dioic acids, alcohols and compounds having combinations of alcohols and acids are versatile chemical intermediates useful as raw materials for the preparation of adhesives, fragrances, polyamides, polyesters, and antimicrobials. While chemical routes for the synthesis of long-chain $\alpha,\omega$-dicarboxylic acids are available, the synthesis is complicated and results in mixtures containing dicarboxylic acids of shorter chain lengths. As a result, extensive purification steps are necessary. Chemical synthesis is the preferred route of synthesis for these compounds today.

Picataggio reports conversion of the dodecane (a C12 linear alkane) and tetradecane (a C14 linear alkane) or their corresponding fatty acids (dodecanoate, tetradecanoate) into their corresponding $\alpha,\omega$-diacarboxylic acids using the yeast *Candida tropicalis* (see, e.g., Picataggio, et al., *Biotechnology* 10:894-898, 1992). The method described is greatly disadvantaged by its reliance upon exogenous addition of C12 or C14 alkane, or C12 or C14 fatty acid; moreover, the method is disadvantaged by the inability of *Candida* to convert other, non C12 or C14, fatty acid and alkane substrates into corresponding diacids. Thus, a method for the endogenous production of fatty acid substrates of desired chain length and subsequent omega oxidation of the substrates, producing the corresponding $\omega$-hydroxy fatty acid or $\alpha,\omega$-dicarboxylic acid, would provide an economical, competitive route to valuable $\alpha,\omega$-dicarboxylic acids, $\omega$-hydroxy fatty acids, diamines, etc that has no precedence.

Thus, there remains a need for methods and materials for biocatalytic conversion of feedstock chemicals into their corresponding $\omega$-hydroxy fatty acids and $\alpha,\omega$-dicarboxylic acids, methods for producing the $\omega$-hydroxy fatty acid and $\alpha,\omega$-diacarboxylic acid in a fermentation broth, methods for controlling the $\omega$-hydroxy fatty acid or $\alpha,\omega$-dicarboxylic acid or fatty acid chain length, methods for secreting or retaining the product from/in the cells, and methods for purifying the product from the culture broth. The present invention meets these needs.

SUMMARY OF THE INVENTION

This present invention provides recombinant host cells and related methods and materials for the biocatalytic production of $\alpha,\omega$-dicarboxylic acids, $\omega$-hydroxy fatty acids, fatty acids (FA), or other fatty acid-derived molecules from fermentable carbon sources and provides a source of diacids for the production of renewable chemicals for use in applications, including making polyesters, resins, polyamides, nylon, fuel additives and fuels, lubricants, paints, varnishes, engineering plastics and the like.

The invention provides host cells and methods for producing fatty acids, $\omega$-hydroxy fatty acids, $\alpha,\omega$-dicarboxylic acids, and related compounds with controlled chain lengths from inexpensive feedstocks, including cornstarch, cane sugar, glycerol, and other carbon sources. The invention also provides methods for making specific short and long chain fatty acids, diacids, and diols that have not previously been made by biosynthetic methods in microbial host cells.

In nature there exist multiple routes for microbial production of fatty acids of different chain lengths. The most abundant in nature are the fatty acid pathways, of which there are three primary systems: the Type I, Type II, and Type III fatty acid systems. Type I and Type III fatty acid systems often contain multiple enzymatic activities on a single polypeptide chain and are referred to as elongases for the Type III system. Generally, Type I and Type III systems generate specific chain length acyl-CoA molecules, which are normally transferred directly into the production of membrane lipids (phospholipids, glyerolipids, etc.) but can be hydrolyzed by a thioesterase to release the free fatty acid in engineered systems. Type II fatty acid systems are composed of single polypeptides that individually encode the multiple enzymatic activities required for fatty acid biosynthesis to generate a range of fatty acyl-ACPs that are normally transferred directly into the production of membrane lipids, but can be hydrolyzed by a thioesterase that recognizes specific chain length fatty acids.

Certain cells also make molecules called polyketides that contain aliphatic backbones similar to fatty acids. Certain of these polyketides are made by Type I polyketide synthases (PKSs). Type I PKSs are composed of catalytic modules that minimally contain an acyl carrier protein (ACP), acyl transferase (AT), and a ketosynthase (KS) and in some instances contain a ketoreductase (KR), a KR and a dehydratase (DH), and a KR, DH, and an enoyl reductase (ER). Type I PKSs generally contain a thioesterase (TE) to cleave the product from the acyl-ACP thioester, unlike natural fatty acid systems that directly incorporate acyl-ACPs or acyl-CoAs through transfer reactions. In Type I PKSs, the starter molecule and the total number of extension modules dictates the length of the final product. Type I PKSs' modular nature has made them amenable to engineering a variety of products not made by naturally occurring PKSs.

The enzymatic decarboxylation of a 2-keto acid substrate results in the formation of the corresponding aliphatic aldehyde; subsequent oxidation of the aldehyde to the corresponding carboxylic acid produces the corresponding fatty acid. All cells make a variety of 2-keto acids as intermediates in amino acid biosynthesis. Cells engineered for overexpression of native or engineered enzymes encoded by genes in the LeuABCD operon (for example, and without limitation, in *E. coli*) extend by a single carbon the 2-keto acid substrate 2-ketobutyrate into longer chain length 2-keto acids.

In accordance with the methods of this invention, engineered cells and recombinant vectors are provided in which Type I, II, III fatty acid synthases, Type I PKSs, and 2-ketoacid biosynthesis pathways, decarboxylases, and oxidases are genetically engineered to make free fatty acids of a specific chain length.

In various embodiments of the host cells and recombinant DNA vectors of the present invention, Type I PKS systems are engineered to produce a specific chain length fatty acid by choosing the appropriate number of modules that terminate with a thioesterase that cleaves the thioester bond and releases a free carboxylate. This thioesterase can be covalently attached to the PKS polypeptide, or expressed independently. In other embodiments of the present invention, a recombinant Type I fatty acid system is employed to produce fatty acid. The FA biosynthesis enzymes produce a specific chain length acyl-thioester, and a thioesterase is used to produce a fatty acid for subsequent oxidation to the dicarboxylic acid. In other embodiments of the invention, a type II fatty acid system is employed to produce fatty acid, thioesterases specific for desired chain lengths are employed to produce the desired chain length fatty acid product. In other embodiments of the invention, a Type III fatty acid system is employed to produce specific chain length fatty acid coenzyme A (CoA) esters, and a thioesterase is employed to cleave the specific chain length fatty acid from CoA. In other embodiments of the present invention, a Type I hybrid PKS system is employed to produce a desired chain length fatty acid, where the C-terminal PKS domain is a thioesterase that cleaves the fatty acid from the acyl carrier protein. In yet other embodiments of the present invention, a 2-keto acid pathway, 2-keto acid decarboxylase, and aldehyde dehydrogenase are used to produce a desired chain length fatty acid.

Numerous microbes can be employed for the production of fatty acid-derived chemicals in accordance with the methods of the invention. In various embodiments, the microbes have characteristics that allow them to produce higher levels of product. For example, in one embodiment, the host organism provided by the invention lacks or has reduced expression levels of, or has been modified for decreased activity of, enzymes catalyzing the degradation of specific chain length fatty acids. These enzyme activities include CoA-ligases (for example, and without limitation, FadD (*E. coli*), FAA1, FAA2, FAA3, FAA4 (*S. cerevisiae*), etc as provided later and enzymes necessary for beta oxidation of fatty acids (for example, and without limitation, POX1, POX2, IDP3, TES1, FOX3 (*S. cerevisiae*), etc as provided later). In some embodiments of the present invention, diols are produced from fatty acids. In these embodiments, enzymes necessary for beta oxidation will be reduced, but CoA-ligases may be retained.

Because malonyl-CoA is an essential precursor to fatty acid synthesis, it is advantageous to upregulate malonyl-CoA biosynthesis. In various embodiments of the invention, the host organism has been engineered for increased expression of enzymes catalyzing production of malonyl-CoA. For example, and without limitation, increasing the expression level of actyl-CoA carboxylase (gene ACC1 (FAS3) in *S. cerevisiae* is included herein for reference).

Thus, the invention provides a variety of different engineered host organisms that exhibit improved production of fatty acids and the corresponding diacid products. In various embodiments, the host organisms have reduced expression of genes and/or their corresponding enzyme products associated with fatty acid, α,ω-dicarboxylic acid, and related product, beta-oxidation, and have increased expression of genes and/or their corresponding enzyme products associated with α,ω-dicarboxylic acid and related product transporters. In this manner, the organism is deficient in its ability to degrade the final fatty acid or α,ω-dicarboxylic acid product and/or secretes product into the fermentation broth. Furthermore, the organism has been engineered for increased expression of genes and/or their corresponding enzyme products associated with biosynthesis of malonyl-CoA. In some embodiments, the methods of the invention are practiced with host cells in which the genes/enzymes that promote storage of fatty acids and so impede the ability to achieve high production levels of a given fatty acid derived product have been inactivated or engineered to reduce expression level/activity.

In some embodiments, the host organism is yeast. Yeast host cells suitable for practice of the methods of the invention include, but are not limited to, *Yarrowia*, *Candida*, *Bebaromyces*, *Saccharomyces*, *Schizosaccharomyces* and *Pichia*, including engineered strains provided by the invention. In one embodiment, the yeast host cell is a species of *Candida*, including but not limited to *C. tropicalis*, *C. maltosa*, *C. apicola*, *C. paratropicalis*, *C. albicans*, *C. cloacae*, *C. guillermondii*, *C. intermedia*, *C. lipolytica*, *C. panapsilosis* and *C. zeylenoides*. In one embodiment, *Candida tropicalis* is the host organism.

In some embodiments the host is bacteria. Bacterial host cells suitable for practice of the methods of the invention include, but are not limited to, *Escherichia* and *Bacillus*, including engineered strains provided by the invention. In one embodiment, the bacterial host cell is a species of *Bacillus*, including but not limited to *B. subtilis*, *B. brevis*, *B. megaterium*, *B. aminovorans*, and *B. fusiformis*. In one embodiment, *B. subtilis* is the host organism.

In the methods of the present invention, once a fatty acid of a desired chain length is produced, it is hydroxylated at the omega carbon to produce a ω-hydroxy fatty acid. In many embodiments, the hydroxylation is achieved by expressing a cytochrome P450 or monooxygenase that is specific for hydroxylation at the terminal (omega, ω-) carbon of a fatty acid (EC 1.14.15.3). ω-hydroxy fatty acids are themselves valuable and are used in the production of fast drying paints and varnishes, etc. As such, the methods of the invention provide that, if desired, the ω-hydroxy fatty acid can be isolated. Alternatively, the omega-hydroxy fatty acid is then, in accordance with the methods of the invention, further oxidized to a α,ω-dicarboxylic acid. In various embodiments, the route of oxidation is through an aldehyde, mediated by either a fatty alcohol dehydrogenase (FAD) or fatty alcohol oxidase (FAO) (these two terms are used interchangeably; EC 1.1.3.20 or 1.1.3.13). The aldehyde intermediate is then converted into a diacid by an aldehyde dehydrogenase (ADH; EC 1.2.1.3 or 1.2.1.4). In some embodiments, the P450 monoxygenase carrying out hydroxylation of the omega carbon is P450 BM3 from *B. megaterium*, either wild type or engineered for altered regiospecficity; for example, without limitation, introduction of mutation of phenylalanine 87 to alanine (mutation F87A) in P450 BM3 alters enzyme regiospecificity toward increased hydroxylation of fatty acid substrates at the omega position (Oliver et al, *Biochemistry*, 36:1567-1572, 1997).

FIG. 1 shows various biosynthetic reactions provided by the method of the invention. Using the Type I, II, or III fatty acid synthase by the method of the invention, a desired fatty acid is produced intracellulary, hydroxylated by a cytochrome P450 at the omega carbon, and then enzymatically oxidized to the α,ω-dicarboxylic acid. Using the Type I PKS by the method of the invention, a desired fatty acid is produced from the PKS system by appropriate selection of the acyl-CoA loading module, extension modules, and thioesterase; the resulting fatty acid is subsequently hydroxylated by a fatty acid omega hydroxylase (EC 1.14.15.3), and oxidized to the corresponding α,ω-dicarboxylic acid by an alcohol oxidase (EC 1.1.3.20 or 1.1.3.13) and aldehyde dehydrogenase (EC 1.2.1.3 or 1.2.1.4).

FIG. 4 shows a 2-keto acid-based pathway to production of the α,ω-dicarboxylic acid adipic acid. By the method of the invention, 2-ketoheptanoate is produced from the naturally occurring substrate 2-ketobutyrate in the host organism through the activity of enzymes encoded by the LeuABCD operon genes. 2-ketoheptanoate is subsequently decarboxylated to 1-hexanal throught the activity of the KivD decarboxylase, oxidized to the fatty acid by aldehyde dehydrogenase (EC 1.2.1.3), to the ω-hydroxy fatty acid by a fatty acid omega hydroxylase (EC 1.14.15.3), and to the α,ω-dicarboxylic acid adipate by an alcohol oxidase (EC 1.1.3.20 or 1.1.3.13) and aldehyde dehydrogenase (EC 1.2.1.3 or 1.2.1.4).

Thus, the invention provides new pathways for making α,ω-dicarboxylic acids in modified host cells. While all yeast, *E. coli*, and *Bacillus* hosts have endogenous routes to production of the α,ω-dicarboxylic acid succinate, no other α,ω-dicarboxylic acids are produced in unmodified host cells. In one aspect, the present invention provides a method for producing one or more fatty acid-derived dicarboxylic acid compounds in a genetically modified host cell that does not naturally produce the α,ω-dicarboxylic acid compounds. For example, and without limitation, yeast and *E. coli* hosts do not make α,ω-dicarboxylic acids by the methods of this invention. *Bacillus* is not known to naturally produce any α,ω-dicarboxylic acids, except pimelic acid, by the methods of the invention; furthermore, the methods of the invention provide additional routes to other diacids in a *Bacillus* host.

In one aspect, the present invention provides methods for the biosynthesis of fatty acid derived α,ω-dicarboxylic acids compounds ranging in carbon length from C3 to C26, including both even and odd numbers of carbons. Such α,ω-dicarboxylic acid compounds include, but are not limited to, C3 diacids, C4 diacids, C5 diacids, C6 diacids, C7 diacids, C8 diacids, C9 diacids, C10 diacids, C11 diacids, C12 diacids, C13 diacids, C14 diacids, C15 diacids, C16 diacids, C17 diacids, C18 diacids, C19 diacids, C20 diacids, C21 diacids, C22 diacids, C23 diacids, C24 diacids, C25 diacids, and C26 diacids.

In other embodiments of the invention, the methods for producing ω-hydroxy fatty acids are provided. In these embodiments of the invention, appropriate selection of the P450 enables hydroxylation of the free fatty acid at the ω-position. For example, and without limitation, expression of native P450 BM3 results in mixed hydroxylation of numerous fatty acid substrates at the ω-1, ω-2 and ω-3 positions; introduction of the point mutation F87A into the P450 BM3 amino acid sequence imparts ω-hydroxylation regioselectivity when using various fatty acid substrates. As described in the preceding paragraph, such ω-hydroxy fatty acid compounds include, but are not limited to, C3 to C26 ω-hydroxy fatty acids.

One can modify the expression of a gene by a variety of methods in accordance with the methods of the invention. Those skilled in the art would recognize that increasing gene copy number, ribosome binding site strength, promoter strength, and various transcriptional regulators can be employed to alter an enzyme expression level. The present invention provides a method of producing a fatty acid derived α,ω-dicarboxylic acid compounds in a genetically modified host cell that is modified by the increased expression of one or more genes involved in the production of fatty acid compounds, such that the production of fatty acid compounds by the host cell is increased. The invention also provides such genetically modified host cells. Such genes include, without limitation, those that encode the following enzymatic activities: acetyl CoA carboxylase, ketosynthase, ketoreductase, dehydratase, enoyl reductase, cytosolic thioesterase, and acyl-carrier protein. Illustrative genes that encode these enzymatic functions include acpP, acpS, accA, accB, accC, accD, fabD, fabH, fabG, fabZ, fabA, fabI, fabB, fabF (suitable copies of these genes may be obtained from, and without limitation, *E. coli, B. subtilis*), tesA, tesB (*E. coli*), yneP, ysmA, ykhA, yvaM, ylpC (*B. subtilis*), FAS1, FAS2, FAS3, ELO1, ELO2, ELO3 (*S. cerevisiae*), ELO1, ELO2, ELO3 (*T. brucei, T. cruzi, L. major*), fasA, fasB (*C. glutamicum, B. ammoniagenes, C. ammoniagenes*), FAS1 (*Mycoplasma tuberculosis, Mycoplasma. smegmatis*), and hexA, hexB (*A. flavus, A. parasiticus*). In other embodiments, one increases transcriptional regulation of these genes. Suitable transcriptional regulators include fadR (suitable copies of these genes may be obtained from, and without limitation, *E. coli* or *B. subtilis*) and RAP1, ABF1, REB1, INO2, INO4 (*S. cerevisiae*).

The present invention also provides a method of producing a fatty acid derived α,ω-dicarboxylic acid compound in a genetically modified host cell that is modified by the decreased or lack of expression of one or more genes encoding proteins involved in the storage and/or metabolism of fatty acid compounds, such that the storage and/or metabolism of fatty acid compounds by the host cell is decreased. Such genes include, without limitation, the following: the acyl-CoA sterol transferases ARE1 (*S. cerevisiae*), ARE2 (*S. cerevisiae*), diacylglycerol acyl transferases, DGA1 (*S. cerevisiae*) and LRO1 (*S. cerevisiae*), plsB, plsX (*E. coli*), yhfL, lcfA, des, plsX, cypC, and yhfT (*B. subtilis*) genes.

The present invention also provides methods and host cells that have been engineered to be capable of secreting or excreting the product into the media. In one embodiment, engineered host cells and methods are provided to make fatty acids that are secreted or excreted into the fermentation broth. In particular embodiments, these genetically modified host cells are modified by expression of one or more genes encoding proteins involved in the export of α,ω-dicarboxylic acid, fatty acid, or ω-hydroxy fatty acid compounds such that the product is moved from the interior of the cell to the exterior. Such genes include the following: DAL5, DIP5, JEN1 (*S. cerevisiae*), MAE1 (*Schizosaccharomyces pombe*), atoE, citT (*B. subtilis*), dcuB, dcuC (*B. subtilis, A. succinogenes, E. coli*), and various multidrug resistance pumps.

Once in the fermentation broth, the diacids and hydroxy acids can be separated and purified in accordance with the invention. In various embodiments of the invention, the microbe is engineered to secrete fatty acids, α,ω-dicarboxylic acids, or ω-hydroxy fatty acids and subsequently purified from the broth. In various embodiments of the invention, the products are purified through precipitation as calcium salts, or reactive extraction with tertiary amines. In various embodiments of the invention, the tertiary amines employed include, and without limitation, tripropylamine, trioctylamine, or tridecylamine. In some embodiments of the invention, ion exchange is employed for further purification of the fatty acid, α,ω-dicarboxylic acid, or ω-hydroxy fatty acid.

In other embodiments, the host cells are not engineered or modified to secrete the product into the growth medium and the product accumulates in the host cell. In these embodiments, the diacid product is separated from the host cell in accordance with the invention by centrifugation or settling of the cell material, cell lysis, and subsequent purification of the diacid product as described above.

Thus, the present invention further provides for a wide variety of genetically modified host cells useful in practice of the methods of the present invention. In various embodiments, the host cell is genetically modified in any one of and any combination of the genetic modifications described herein.

The present invention further provides for an isolated dicarboxylic acid compound produced from the methods of the present invention.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1 depicts a progression that shows the flow of carbon from a feedstock such as sugar, through a FA node to form specific chain length FAs, which are then oxidized at the ω carbon to produce ω-hydroxy-FAs, ω-oxo-FAs, and finally, α,ω-dicarboxylic acids. Enzymes are italicized and major producted are indicated in bold.

FIG. 2A is compiled data from MS analysis to identify tetradecanoic acid, 13- or 14-hydroxy-tetradecanoic acid, and tetradecanedioic acid from cultures expressing P450 Bm3 alone or cultures coexpressing a thioesterase, LtesA and P450 Bm3s. There is no detectable product for cultures expressing Bm3 alone, but there is production of tetradecanoic acid, 13- or 14-hydroxy-tetradecanoic acid, and tetradecanedioic acid in cultures expressing the P450 Bm3 and LtesA. FIG. 2B is data showing the identification of the molecular ion for tetradecanedioic acid from the MS data for cultures expressing both the P450 Bm3 and LtesA.

DETAILED DESCRIPTION OF THE INVENTION

Figure 1:
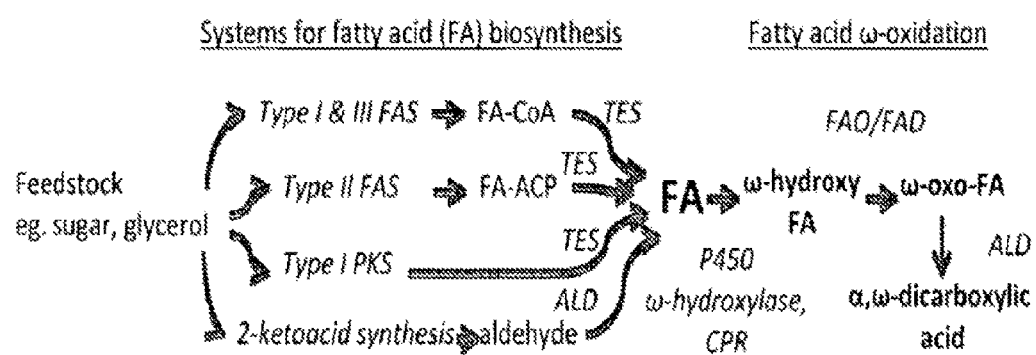
FIG. 1 illustrates five of the general α,ω-dicarboxylic acid production methods of the present invention. A summary of the engineered pathways for production of fatty acids from Type I, Type II, and Type III FAS, Type I PKS, and 2-ketoacid synthesis is provided. Fatty acids of the desired chain length are produced using Type I, Type II, or Type III fatty acid synthase systems or Type I hybrid PKS systems, or decarboxylation and oxidation of 2-ketoacids. The resulting fatty acid is subsequently oxidized to the corresponding α,ω-dicarboxylic acid by fatty acid a fatty acid omega hydroxylase (EC 1.14.15.3), fatty alcohol oxidase (1.1.3.20 or 1.1.3.13), and aldehyde dehydrogenase (1.2.1.3 or 1.2.1.4).

Before the invention is described in detail, it is to be understood that, unless otherwise indicated, this invention is not limited to particular nucleic acids, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be (or has been) transformed via insertion of an expression vector. Thus, a host organism or cell as described herein may be a prokaryotic organism (e.g., an organism of the kingdom Eubactera) or a eukaryotic cell. As will be appreciated by one of ordinary skill in the art, a prokaryotic cell lacks a membrane-bound nucleus, while a eukaryotic cell has a membrane-bound nucleus.

As used herein, a "recombinant cell" or "recombinant host cell" refers to a host cell that has been genetically altered to comprise a heterologous nucleic acid sequence. Such a heterologous sequence may be: (i) an exogenous nucleic acid that is not native to the cell, e.g., an exogenous gene, an exogenous promoter, an optimized coding sequence, a mutated coding sequence; (ii) extra copies of an endogenous gene or promoter; (iii) or nucleic acids, e.g., a promoter operably linked to a coding region, that are heterologous to one another. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "heterologous nucleic acid" or "heterologous DNA" as used herein refers to a polymer of nucleic acids wherein at least one of the following is true: (a) the sequence of nucleic acids is exogenous to (i.e., not naturally found in) a given host microorganism (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. For example and without limitation, the present invention describes the introduction of an expression vector into a host microorganism, wherein the expression vector contains a nucleic acid sequence coding, e.g., a promoter and/or coding region, that is not normally found in a host microorganism. With reference to the host microorganism's genome, then, the nucleic acid sequence is heterologous.

The terms "expression vector" or "vector" refer to a nucleic acid compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing normucleotidic backbones, provided that the polymers contain nucleobases in a configuration that allows for base pairing and base stacking, as found in DNA and RNA. As used herein, the symbols for nucleotides and polynucleotides are those recommended by the IUPAC-IUB Commission of Biochemical Nomenclature (Biochem. 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

Figure 4:
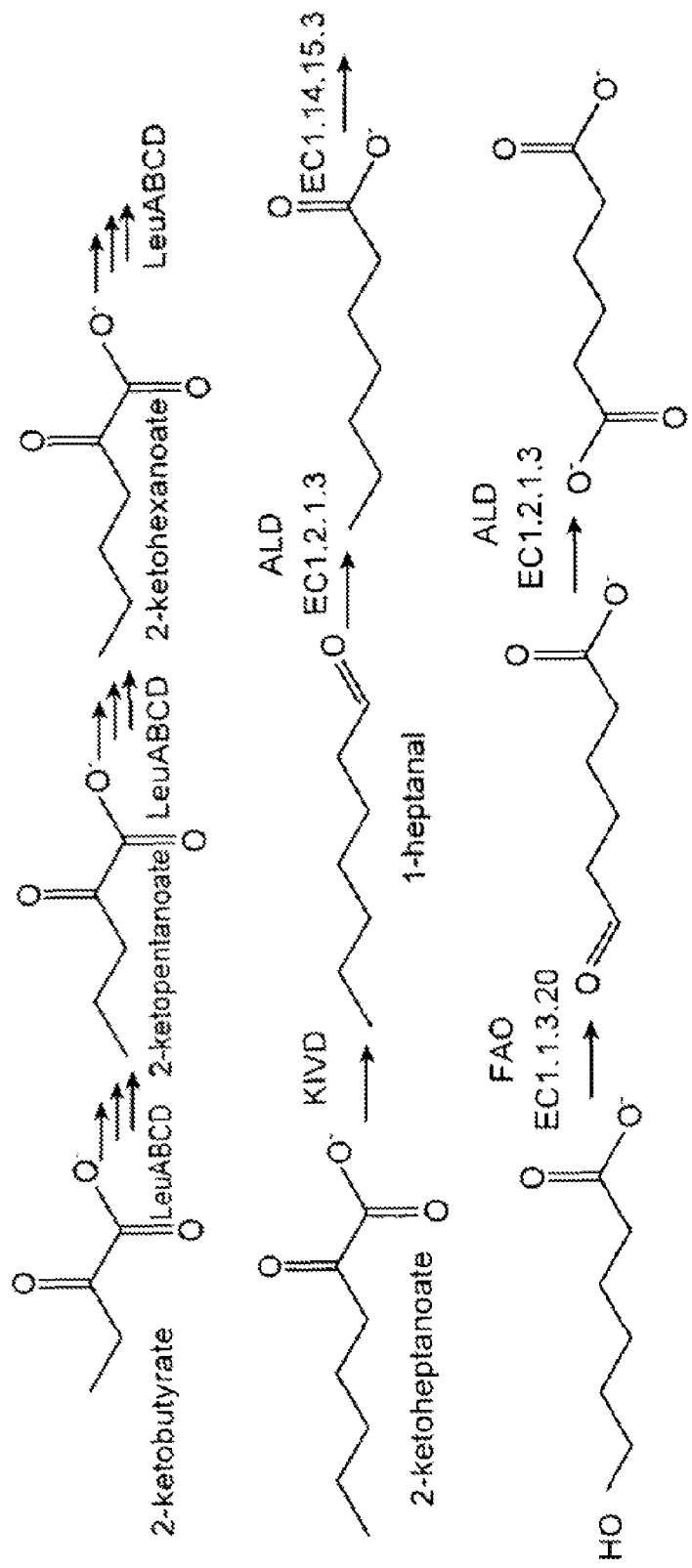
FIG. 4 illustrates use of a 2-ketoacid pathway for the production of an α,ω-dicarboxylic acid (e.g., adipate) in accordance with an embodiment of the invention. Similar short-chain α,ω-dicarboxylic acids can be produced by varying the 2-ketoacid overproduced in the host cell. Following decarboxylation of the fatty acid with substrate promiscuous KivD decarboxylase, or other related decarboxylases (EC 4.1.1.X), the resulting fatty acid is subsequently oxidized to the corresponding α,ω-dicarboxylic acid by a fatty acid omega hydroxylase (EC 1.14.15.3), alcohol oxidase (1.1.3.20 or 1.1.3.13), and aldehyde dehydrogenase (1.2.1.3 or 1.2.1.4).

In some embodiments, the invention provides for a method for producing a $\alpha,\omega$-dicarboxylic acid in a genetically modified host cell, the method comprising: culturing a genetically modified host cell under a suitable condition to produce enzymes in a system to oxidize fatty acids to $\omega$-hydroxy fatty acids to $\alpha,\omega$-dicarboxylic acids. In some embodiments, such a genetically modified host cell comprises first a enzyme that produces a fatty acyl-CoA (or acyl-ACP), a second optional enzyme that is a thioesterase, an fatty acid omega oxidase (EC 1.14.15.3) that oxides the fatty acid at the $\omega$-carbon to produce a $\omega$-hydroxy fatty acid, a second oxidase, i.e., a fatty alcohol dehydrogenase (FAD) or fatty alcohol oxidase (FAO) (these two terms are used interchangeably; EC 1.1.3.20 or 1.1.3.13), to oxidize the $\omega$-hydroxy fatty acid to an aldehyde, and an aldehyde dehydrogenase (ADH; 1.2.1.3 or 1.2.1.4) to convert the aldehyde into an $\alpha,\omega$-dicarboxylic acid. Again, the methods of the invention are generally illustrated in FIG. 1 and involve either Type I, II, or III fatty acid synthase systems, or a Type I PKS system or a 2-ketoacid system, wherein the carbon length of the output fatty acid is controlled. FIG. 4 illustrates the extension of endogenously produced 2-ketybutyrate substrate to longer chain 2-ketoacids throught the activity of enzymes encoded by the LeuABCD operon, subsequent decarboxylation to the fatty aldehyde, and oxidation to the fatty acid. In various embodiments, appropriately selected oxidizing enzymes perform omega oxidation on said fatty acid.

In some embodiments, the genetically modified host cell comprises a first nucleic acid construct encoding the first enzyme (i.e., the elongase), optionally a second nucleic acid construct encoding the thioesterase, a third nucleic acid encoding the fatty acid omega hydroxylase, a fourth nucleic acid encoding the FAD or FAO and a fifth nucleic acid encoding the ADH, and the culturing results in the expression of the elongase, (optionally) the thioesterase, the fatty acid omega hydroxylase, the FAD or FAO and the ADH.

In some embodiments, the method further comprises the step of recovering the diacid produced, wherein the recovering step is concurrent or subsequent to the culturing step. Kurzrock et al, report on multiple purification strategies used for isolation of the microbially produced diacid succinate from fermentation broth (Kurzrock et al. *Biotechnology Letters,* 32:331-339, 2010); these methods, including precipitation with calcium hydroxide, calcium oxide, or ammonia; electrodialysis; reactive extraction with long chain aliphatic primary, secondary, or tertiary amines (for example, and without limitation, tripropylamine, trioctylamine, or tridecylamine) in organic solvent; and ion exchange are generally applicable for purification of fatty acid, $\alpha,\omega$-dicarboxylic acid, $\omega$-hydroxy fatty acids products. In various embodiments of the invention, the products are purified through precipitation as calcium salts, or reactive extraction with tertiary amines. In various embodiments of the invention, the tertiary amines employed include, and without limitation, tripropylamine, trioctylamine, or tridecylamine. In some embodiments of the invention, ion exchange is employed for further purification of the fatty acid, α,ω-dicarboxylic acid, or ω-hydroxy fatty acid.

In various embodiments, the method comprises a method of genetically modifying a cell, e.g., a bacterial or yeast cell, to increase expression of one or more genes involved in the production of fatty acid compounds; such that the production of fatty acid compounds by the cell is increased. Such genes encode proteins such as acetyl-CoA carboxylase (ACC), cytosolic thioesterase (LtesA), a fatty acid synthase, and acyl-carrier protein (AcpP). In some embodiments, the genetically modified cell may be modified to produce higher levels of cytosolic acetyl-coA and malonyl-CoA. Thus, in some embodiments a genetically modified cell may comprise a modification to express, or increase expression of, proteins such as ATP citrate lyase.

In various embodiments, the genetically modified host cell expresses an enzyme system for producing α,ω-dicarboxylic acids from a simple sugar substrate (for example, but not limited to, glucose, sucrose, xylose, arabinose; such sugars might be obtained from cornstarch, sugar cane, cellulosics, and waste biomass), wherein the enzyme system comprises: an elongase to produce a fatty-acyl-CoA-thioester of a desired chain length; a fatty acid omega hydroxylase (EC 1.14.15.3) to hydroxylate the fatty acid at the omega carbon to produce a ω-hydroxy fatty acid; an oxidase to oxidize the ω-hydroxy fatty acid to an aldehyde (EC 1.1.3.20 or 1.1.3.13); and an aldehyde dehydrogenase to produce the α,ω-dicarboxylic acid (EC 1.2.1.3 or 1.2.1.4); and wherein at least one of the enzymes are recombinant enzymes encoded by one or more expression cassettes.

In various embodiments, the genetically modified host cell expresses an enzyme system for producing α,ω-dicarboxylic acids from a simple sugar substrate (for example, but not limited to, glucose, sucrose, xylose, arabinose; such sugars might be obtained from cornstarch, sugar cane, cellulosics, and waste biomass) wherein the enzyme system comprises: an elongase to produce a fatty-acyl-CoA-thioester of a desired chain length; a thioesterase that produces a fatty acid from the acyl-thioester; an oxidase to hydroxylate the fatty acid at the omega carbon to produce a ω-hydroxy fatty acid (EC 1.14.15.3); an oxidase to oxidize the ω-hydroxy fatty acid to an ω-oxo fatty acid (EC 1.3.20 or 1.1.3.13); and an aldehyde dehydrogenase to produce the α,ω-dicarboxylic acid (EC 1.2.1.3 or EC 1.2.1.4), wherein at least two of the enzymes are recombinant enzymes encoded by one or more expression cassettes.

Enzymes and Constructs Encoding Thereof

As noted above, one of the advantages of the present invention is that it does not rely upon exogenous alkanes, fatty acids (FA), or hydroxy-FA supplementation or the ability of the microbe to produce enough substrate for conversion into diacids (or other products). Instead, in the methods of the present invention, the fatty acid starting material is also microbially produced. Numerous methods for microbially producing fatty acids are known to those of skill in the art and include those methods described in PCT International Publication Nos. WO 2007/136762, WO 2008/100251 and WO 2010/075483 as well as those methods described in U.S. Patent Application Publication No. US 2010/0170148, the teachings of all of which are incorporated herein by reference. Both Type I, II, and III FASs and Type I PKS are employed in various embodiments of the methods of the present invention.

While the invention provides modified host cells, methods and enzymes for the production of fatty acid molecules via five distinct routes but without limitation and including Type I, II and III fatty acid, Type I PKS and 2-ketoacid biosynthetic pathways, first we focus on enzymes involved in fatty acid biosynthesis. Table 1, below, provides Type I, II, and III fatty acid synthases and elongases and other enzymes involved in the biosynsthesis of fatty acids suitable for use or alteration in accordance with the methods and in the host cells of the invention.

In Table 1 below we provide suitable enzymes, without limitation, for performing the methods in accordance with the invention that are used to produce fatty acids via Type I, II or III fatty acid biosynthesis. In detail, the "enzyme" column provides both the gene, enzyme name and its accession number either in NCBI, Genbank, UniProt, or associated catalytic activity, unless the gene name is unavailable in which case only enzyme function and accession numbers are provided. The "modification" column describes the genetic modification in accordance with the invention; "OE" means overexpress and in some embodiments of the invention, where the host cell does not have an endogenous copy of the gene it is taken to mean the enzyme is expressed heterologously. In other embodiments, in which the host cell has an endogenous copy of the gene the gene product is overexpressed. Express and overexpress mean that enzyme levels and activity are increased compared to the wild-type case and those skilled in the art appreciate that this can be achieved by increasing the strength or changing the type of the promoter, increasing the strength of the ribosome binding site or Kozak sequence, increasing the stability of the mRNA transcript, altering the codon usage, and increasing the stability of the enzyme, etc. In the modification column, "decrease" means that the enzyme activity is decreased compared to the wildtype. Those skilled in the art will appreciate that decreasing enzyme activity compared to wildtype is achieved in a variety of ways in accordance with the methods of the invention and not limited to completely removing an enzyme by gene knockout, addition of an inhibitor compound that reduces or eliminates enzyme's activity, expression level is modulated such that total enzyme activity is decreased by weakening a promoter, ribosome binding site or Kozak sequence, by decreasing mRNA transcript stability or by increasing protein degradation. The "use" column indicates a more specific use of the enzyme without limitation in accordance with the methods of the invention and in some cases indicates the fatty acid chain length product. For example, the "hexA" enzyme is involved in producing a fatty acid chain six carbons in length and this is indicated by "C6". The "organism" column indicates suitable sources for the genes and enzymes and does not necessarily indicate the choice of host cells. Finally, superscripted numbers indicate relevant citations.

TABLE I

ENZYMES INVOLVED IN FATTY ACID SYNTHESIS
OE = overexpress; Organism = an illustrative, non-limiting organism that is a source of the gene/enzyme

| Gene names that encode enzyme | Modification | Use | Organism |
|---|---|---|---|
| FAS3 (Acetyl-CoA carboxylase; NP_014413.1) | OE | C3 | S. cerevisiae |
| FAS2 (α-subunit of fatty acid synthase; NP_015093.1) | OE | C16, C18 | S. cerevisiae |

TABLE I-continued

ENZYMES INVOLVED IN FATTY ACID SYNTHESIS
OE = overexpress; Organism = an illustrative, non-limiting organism that is a source of the gene/enzyme

| Gene names that encode enzyme | Modification | Use | Organism |
|---|---|---|---|
| FAS1 (β-subunit of fatty acid synthase; NP_012739.1) | OE | C16, C18 | S. cerevisiae |
| ACB1 (acyl-coA binding protein; NP_011551.1) | OE | Sequesters fatty acyl-CoAs | S. cerevisiae |
| ELO1 (elongase I; XP_824876) | OE | C10 | T. brucei[13] |
| ELO1 (XP_813972) | OE | C10 | T. cruzi |
| Beta keto acyl synthases & elongases (CAJ02963, CAJ02967, CAJ02975, CAJ02982, CAJ02986, CAJ03003, CAJ03006, CAJ03013, CAJ03016, CAJ03023, CAJ03028, CAJ03035, CAJ02037, CAJ08636) | OE | C10-C22 | L. Major |
| ELO2 (elongase II; NP_009963) | OE | C22 | S. cerevisiae |
| ELO2 (elongase II; XP_824877) | OE | C14 | T. brucei[13] |
| ELO3 (elongase III; NP_013476) | OE | C26 | S cervisiae |
| ELO3 (elongase III; XP_824878) | OE | C18 | T. brucei[13] |
| ELO4 (elongase IV; XP_824041) | OE | C22 | T. brucei[13] |
| HexA (fatty acid synthase II; AF391094) | OE | C6 | A. flavus, A nomius |
| HexA (fatty acid synthase II; AF391094) | OE | C6 | A. parasiticus, A. flavus |
| HexB (fatty acid synthase I; AY510454) | OE | C6 | A. nomius |
| FAS2 (fatty acid synthase II; AY371490) | OE | C6 | A. parasiticus |
| ERG 10 (thiolase; NP_015297) | OE | C4 | S. cerevisiae |
| atoB (thiolase; NP_416728) | OE | C4 | E. coli |
| phaA (thiolase; YP_353824) | OE | C4 | R. sphaeroides, R. eutropha |
| phaB (acetoacetyl-CoA reductase; NC_014307) | OE | N/A | R. solanacearum |
| Hbd (acetoacetyl-CoA reductase; YP_001307783) | OE | N/A | C. beijerinckii, A. caviae |
| Crt (crotonase; NP_891288) | OE | N/A | C. beijerinckii |
| phaJ (crotonase;) YP_004715374) | OE | N/A | P. stutzeri, T. denticola |
| Bcd/etfA-B (3hydroxybutyryl-CoA dehydrogenase; NP_349154, NP_349155, NP_349314 | OE | N/A | C. acetobutylicum |
| fabH (ketosynthase; NP_415609) | OE | N/A | E. coli |
| fabHB (ketosynthase; NP_388898) | OE | N/A | B. subtilis |
| fabHA (ketosynthase; NP_389015) | OE | N/A | B. subtilis |
| fabA (3hydroxydecanoyl-ACP dehydrase; NP_415474, NP_388285.2) | OE | N/A | B subtilis, E. coli |
| fabZ (3hydroxydecanoyl-ACP dehydrase; NP_391518.2) | OE | N/A | B subtilis, E. coli |
| fabI (enoyl reductase; NP_389054.2, NP_415804.1) | OE | N/A | B subtilis, E. coli |
| fabB (ketosynthase; NP_416826.1, NP_389016.1) | OE | N/A | B subtilis, E. coli |
| fabF (ketosynthase; NP_389016.1, NP_415613.1) | OE | N/A | B subtilis, E. coli |
| fabG (ketoreductase; NP_389473.1, NP_389732.1, NP_389732.1, NP_390820.1, NP_415611.1, | OE | N/A | B subtilis, E. coli |
| fabD (malonyl-CoA transacylase; NP_389472.1, NP_415610.1) | OE | N/A | B subtilis, E. coli |
| acpP (acyl carrier protein; NP_389474.1, NP_415612.1) | OE | N/A | B subtilis, E. coli |
| acpS (phosphopantetheinyl transferase; NP_417058.1, NP_388343.1) | OE | N/A | B subtilis, E. coli |
| DVU2560 (YP_011772.1) | OE | N/A | D. vulgaris |
| fabH (ketosynthase; YP_011773.1) | OE | N/A | D. vulgaris |
| acpP (acyl carrier protein; YP_011774.1) | OE | N/A | D. vulgaris |
| fabF (ketosynthase; YP_011775.1) | OE | N/A | D. vulgaris |

Non-engineered cells typically produce a range of fatty acid chain lengths with varying degrees of saturation to maintain membrane fluidity, etc and usually rely on acyl-transferases to move the fatty acid from the FAS into products that compose cell membranes like diacylglycerols and phospholipids. Under typical conditions, they do not utilize thioesterases as part of the fatty acid biosynthetic machinery and in the case where a fatty acid thioesterase may be present in a naturally occurring organism's genome, they often contain signal peptides that target their expression to areas where fatty acid biosynthesis is not occurring. Therefore, to use the thioesterases in accordance with the methods of the invention, one skilled in the art will appreciate the requirement to express the thioesterase in the same location as where the fatty acids are produced or located. In detail, TesA, a thioesterase native to E. coli has a leader peptide sequence that targets its expression to the periplasm and to use this thioesterase in accordance with the methods of the invention, the sequence must be removed to target its activity to the cytosol (indicated by LTesA) in the case of E. coli, as that is the sight of fatty acid biosynthesis. However, in general, and in the methods in accordance with this invention, thioesterases can be used for cleaving fatty acid moieties whenever the fatty acid is covalently attached via a thioester bond to an acyl-carrier protein and this occurs in most Type II FAS proteins as well as in Type I PKS proteins, while Type I and III FAS proteins typically generate a CoA bound fatty acyl thioester. The distinction here is emphasized because in some cases, the CoA thioester is labile and the fatty acid can be released without a thioesterase, yet, in the other cases, a TE is required to efficiently cleave the thioester bond and release the fatty acid. Although natural hydrolysis may occur in the case of Type I and III FAS proteins (whose composition determines chain length), the rates of hydrolysis in some in bodiments is increased by expressing thioesterases. Another distinction is made between PKS TEs and FAS TEs, because often PKS TEs are incorporated into the PKS polypeptide at the C terminal domain, whereas often FAS TEs are separate proteins, although in the case of FASs this is not a rule. Because PKS TEs are typically this final domain, they will be discussed in a different section, but in some embodiments, a suitable TE is the DEBS TE from the erythromycin PKS pathway. TEs have selectivity for cleaving fatty acyl-CoA or fatty acyl-ACP thioester bonds exist in nature and have been found in a variety of hosts, including but not limited to plants, bacteria and eukaryotes. In accordance with the methods of the invention, for Type I, II, and III fatty acid biosynthesis, a TE with appropriate fatty acid carbon chain length selectivity is chosen for a particular free fatty acid product. While Type I, II, and III FASs and Type I PKSs enzymes utilize TEs, Table II below provides illustrative thioesterases suitably used for the fatty acid synthase systems herein and in accordance with the methods of the invention. To reiterate, in general, many thioesterases are available for use in connection with the fatty acid syntheses, a thioesterase may be used, for example, to produce a fatty acid from either an ACP bound fatty acyl-thioester or to produce a fatty acid from a CoA bound fatty acyl-thioester. Typically with Type II FAS, a thioesterase is employed to cleave the ACP-bound fatty acid. With Type I & III FAS, the fatty-acyl-CoA-thioester is naturally hydrolyzed by water, thereby providing the fatty acid and does not necessarily require a thioesterase.

Thioesterases suitable for use in accordance with the methods of the present invention include those set forth in Table II below. The "thioesterase" column includes the enzyme name and accession number (in most cases) in various forms; the "modification" column is defined as previously, including the operative definition of "OE" or overexpress; substrate specificity refers to the fatty acid chain length recognized by the thioesterase; the "organism" column contains an illustrative organism that is suitable for obtaining the genetic element/enzyme, but is not mean to be limiting.

TABLE II

Thioesterases

| Thioesterases | Modification | Substate specificity | Organism |
|---|---|---|---|
| TesA (NP_415027.1) | OE | C10-C18 | E. coli |
| TesB (NP_414986.1) | OE | C6-C18 | E. coli |
| TES | OE | C12-C18 | R. sphaeroides |
| TES | OE | C6-C18 | R. sphaeroides |
| EST2 | OE | C6 | A. acidocaldarius |
| ESTA | OE | C6 | A. acidocaldarius |
| UcFATB1 (Q41635) | OE | C12 | U. californica |
| chFATB2 (AAC49269) | OE | C8, C10 | C. hookeriana |
| chFATB3 (AAC72881.1) | OE | C14 | C. hookeriana |

In addition to use of thioesterases in the fatty acid pathways described above, the PKS pathways also use thioesterases that in most cases are a part of the PKS peptide located at the C-terminus in accordance with the methods of the invention and are provided in the following. An alternative way of producing the fatty acid of a specific chain length in accordance with the invention is to employ a hybrid PKS. Exemplary modules are listed herein. To make a fully reduced fatty acid of a given chain length, one constructs, in accordance with the invention, a hybrid that contains a loading module (KS, AT, ACP) an extension module (KS, KR, DH, ER, ACP), and a thioesterase (TE). The choice of loading module and choice of extension modules that condense precursors like malonyl-CoA or methylmalonyl-CoA determines whether the fatty acid chain is even or odd carbon number and the number of extension modules preceding the TE determines the overall chain length. To construct an odd-chain fatty acid PKS in accordance with the invention, one selects a loading module that incorporates propionate via methylmalonyl-CoA, and to construct an even-chain fatty acid PKS, one selects a loading module that incorporates acetate via malonyl-CoA. Another method of the invention involves selection of modules that incorporate longer chain acyl-CoA molecules like butyryl-CoA. Illustrative loading, extension, and thioesterase modules suitable for use in the methods, PKS, and host cells of the invention are provided in the following, where a PKS known to produce a specific compound is named followed by parantheticals that identify the source organism for the genetic material.

Non-limiting examples of loading modules for malonyl-CoA are provided as follows: Niddamycin PKS (S. caelestis), Amphotericin PKS (Streptomyces nodosus), Concanamycin a PKS (Streptomyces neyagawaensis), Epothilone PKS (Sorangium cellulosum), Mycolactone PKS (Mycobacterium ulcerans), Nanchangmycin PKS (Streptomyces nanchangensis), Nystatin PKS (Streptomyces noursei), Oleandomycin PKS (Streptomyces antibioticus), Oligomycin (Streptomyces avermitilis), Pimaricin PKS (Streptomyces natalensis), Pyoluteorin PKS (Pseudomonas fluorescens), stigmatellin PKS (Stigmatella aurantiaca).

Non-limiting examples of loading modules for methylmalonlyl-CoA are provided as follows and are used in accordance with the methods of the invention to load an odd-carbon number onto the PKS, but does not necessarily require the final fatty acid product to be an odd-carbon number as described previously: Megalomicin PKS (Micromonospora megalomiceas), Methymycin PKS (Streptomyces venezuelae), Monensin PKS (Streptomyces cinnamonensis), Narbomycin PKS (Streptomyces venezuelae), Neomethymycin PKS (Streptomyces venezuelae), Pikromycin (Streptomyces venezuelae), Spinosad PKS (Saccharopolyspora spinosa), Tylactone PKS (Streptomyces fradiae).

An illustrative example of a loading module for propionyl-CoA is from the erythromycin PKS (Saccharopolyspora erythraea).

Non-limiting extension modules that incorporate malonyl-CoA via condensation, increase the chain length by two carbons, and fully reduce the acyl chain are provided as follows, where "M" and the number indicate the module number within the PKS post loading module, such that "M1" would directly follow a loading module in a given PKS sequence: Nystatin PKS M5, M15 (S. caelestis); Amphotericin PKS M5, M16 (Streptomyces nodosus); Mycolactone PKS M9 (Mycobacterium ulcerans); Nanchangamycin PKS M6, M8 (Streptomyces nanchangensis); Oleandomycin PKS M3 (Streptomyces antibioticus); Stigmatellin PKS M5 (Stigmatella aurantiaca); Soraphen PKS M2, M3, M5 (Sorangium cellulosum); Monensin PKS M6, M8 (Streptomyces cinnamonensis); Spinosad PKS M2 (Saccharopolyspora spinosa); Herbimycin A PKS M6 (S. hygroscopicus); FROO8 PKS M19 (Streptomyces sp. FR-008)

An illustrative example of a thioesterase from the erythromycin PKS (Saccharopolyspora erythraea), which is sometimes referred to as the DEBS TE, is suitable for cleaving the fatty acyl ACP thioester bond produced via PKSs and result in production of a specific chain length fatty acid.

Four major routes to producing a desired chain length fatty acid via Types I, II, or III FASs or Type I PKSs have been described in detail. A fifth route, described below, is through 2-ketoacid intermediates as in a portion of the leucine biosynthetic pathway.

Thus, in another aspect, the present invention provides methods for producing fatty acids, ω-hydroxyacids, and α,ω-dicarboxylic acids (e.g., adipic acid), using elements of amino acid biosynthetic pathways (2-ketoacid system). Normally cells do not produce fatty acids, ω-hydroxyacids, or α,ω-dicarboxylic acids from amino acid pathways. In non-engineered cells, pyruvate in the tricarboxylic acid cycle is converted into oxaloacetate, which is then converted through multiple steps into L-threonine, and then into 2-ketobutyrate via a threonine deaminase. 2-ketobutyrate is normally a substrate in cells for producing isoleucine and leucine, but has also been demonstrated to be a suitable substrate for elongation in one-carbon increments with an engineered LeuA enzyme and native LeuBCD enzymes to produce the 2-ketovalerate (C5), 2-ketocaproate (C6), and 2-ketoheptanoate (C7) intermediates. Suitable mutations of the LeuA enzyme include, but are not limited to, G462D, S139G, H97A, N167A. These ketoacid intermediates are then decarboxylated by a promiscuous enzyme, Kivd (from *Lactococcus lactis*) to form an aldehyde (see, Zhang, et al., "Expanding metabolism for biosynthesis of non-natural alcohols, *Proc Natl Acad Sci USA* 105, 20653-20658 (2008), the teachings of which are incorporated herein by reference). Suitable mutations of the KIVD enzyme include, but are not limited to V461A, F381L.

In accordance with the teaching of the methods of this invention, we convert the fatty aldehyde into a fatty acid by oxidation or expression of an aldehyde dehydrogenase (EC 1.2.1.3). In other embodiments of the invention, we produce a fatty alcohol by expressing an alcohol dehydrogenase (ADH) that converts the aldehyde into an alcohol and serves as a substrate for oxidation to the fatty acid by methods described elsewhere. In some embodiments, a suitable, but not limited to alcohol dehydrogenase is ADH6 (*S. cerevisiae*). The pathway utilized in this embodiment of the invention is illustrated in FIG. 4. Examples of short chain aldehyde dehydrogenases (ALDs) have been described and suitable enzymes are listed below. Further oxidation of the omega-carbon is necessary, once the short chain fatty acid is produced, and is achieved through omega oxidation described in a following section.

To produce a fatty acid from the 2-ketoacid pathway, the supply of the keto acid (e.g., 2-ketobutyrate) is important as a precursor to the pathway, thus in some embodiments the invention provides cells that are engineered to produce appropriate substrate levels by overexpressing genes that encode enzymes in the pathway. The present invention provides a number of ways to supply or increase the supply of 2-ketobutyrate, which ultimately increases the fatty acid, ω-hydroxyfatty acid, or α,ω-dicarboxylic acid product; these include, but are not limited to: threonine degradation pathways, isoleucine biosynthesis pathways (via citramalate synthase and 2-methylmalate), glutamate pathways (via 2-methylaspartate and 2-methyloxaloacetate) or χ-elimination of o-phosphohomoserine and o-acetyl-homoserine. Other host cells and methods of the invention exploit prevention of transamination of ketoacids by deletion or attenuation of various genes including, e.g., ilvE, tyrB, etc.

Here, we provide enzymes without limitation in accordance with the methods of the invention for producing fatty aldehydes, fatty acids, w-hydroxy fatty acids, and diacids from 2-ketoacid precursors. First, we provide the enzymes involved in elongating the 2-ketoacid precursor, 2-ketobutanoate to 2-ketovalerate, 2-ketocaproate, and 2-ketoheptanoate, and decarboxylating these precursors to fatty aldehydes as provided below in Table III, with column definitions as previously described, but with the "EC number" that provides the biochemical reaction associated with the provided enzymes.

TABLE III 2-ketoacid enzymes

| Enzyme | EC Number | Modification | Organism |
| --- | --- | --- | --- |
| leuA | 2.3.3.13 | Overexpress: G462D, S139G, H97A, N167A | *E. coli, B. subtilis* |
| leuB | 1.1.1.85 | OE | *E. coli, B. subtilis* |
| leuC | 4.2.1.33 | OE | *E. coli, B. subtilis* |
| leuD | 4.2.1.33 | OE | *E. coli, B. subtilis* |
| tyrB | 2.6.1.42 | attenuate | *E. coli, B. subtilis* |
| ilvE | 2.6.1.42 | attenuate | *E. coli, B. subtilis* |
| Kivd | | OE | *Lactococcus lactis* |
| ilvA | 4.2.1.16 | OE | *E. coli* |
| tdcB | 4.2.1.16 | OE | *E. coli* |
| CHA1 | | OE | *S. cerevisiae* |
| ILV1 | 4.3.1.9 | OE | *S. cerevisiae* |
| LEU1 | 4.2.1.33 | OE | *S. cerevisiae* |
| LEU2 | 1.1.1.85 | OE | *S. cerevisiae* |
| BAT1, BAT2 | | attenuate | *S. cerevisiae* |

Having provided the enzymes for production of fatty aldehydes from 2-ketoacid pathways in accordance with the methods of the invention, we now provide without limitation enzymes for the conversion of the fatty aldehydes into fatty acids by expressing aldehyde dehydrogenase (ALD) enzymes performing biochemistry described by EC 1.2.1.3 and shown in FIG. 4. In general, many ALDs exist, but here we provide suitable, non-limiting examples by enzyme name and in paranthesis, an illustrative source organism for the enzyme, and any associated specificity as a carbon chain length range (eg C4-C14): Ald1 (*Acinetobacter* sp M1; C4-C14); ScAld1 (*Mus musculus*; C6-C9); Psdr1 (*Homo sapiens*; C2-C12); ALD4 (*S. cerevisiae*; C2-C12), etc. In accordance with the methods of the invention, we have now provided five routes to produce fatty acids with specific carbon chain lengths via the Type I, II, and III FASs, Type I PKSs, and the 2-ketoacid biosynthetic enzymes. In the following, we provide enzymes for the production of ω-hydroxyacids and α,ω-dicarboxylic acids from these fatty acid precursors, but next we describe production of other valuable chemicals from the 2-ketoacid pathways.

In addition to the α,ω-dicarboxylic acids, ω-hydroxyacids, diols and shorter chain monoacids are synthesized using the 2-keto acid pathway in accordance with other embodiments of the invention. For instance, in one embodiment, production of a monoacid is achieved by eliminating reactions EC 1.14.15.3 and EC 1.1.3.20 from the pathway illustrated in FIG. 4. In another embodiment, production of a ω-hydroxyacid is achieved by eliminating reaction EC 1.1.3.20 from the pathway illustrated in FIG. 4. In yet another embodiment, production of a diol is achieved by replacing the ALD (aldehyde dehyrogenase) EC 1.2.1.3 with an aldehyde reductase EC 1.1.1.21 in the pathway illustrated in FIG. 4.

The methods of the present invention involve the use of an oxidase to hydroxylate the fatty acid at the omega carbon to produce a ω-hydroxy fatty acid. As discussed in the background section above, for example *Candida tropicalis* shows the oxidation of the C12 and C14 fatty acid to the C12 and C14 ω-hydroxy fatty acid is described, for example, by Picataggio, et al. (*Biotechnology* 10:894-898, 1992) and in U.S. Pat. Nos. 7,405,063; 7,160,708; 7,109,009; 7,063,972;

7,049,112; 6,790,640; and 6,331,420 as well as in PCT International Publication No. WO 2004/013336, the teachings of all of which are incorporated herein by reference. In one embodiment, productivity of the ωoxidation is enhanced by amplification of both the cytochrome P450 monooxygenase and NADPH- or NADH-cytochrome reductase genes or by using highly active promoters with such genes.

Once the fatty acid of a desired chain length is produced with one of the five routes it is hydroxylated in accordance with the invention at the omega carbon, producing a ω-hydroxyfatty acid. ω-hydroxyfatty acids themselves are valuable and used in the production of rapidly drying paints and varnishes, etc.

Here, we provide without limitation and in accordance with the methods of the invention enzymes that are suitable for overexpressing in the provided host cells and results in hydroxylating the omega carbon to produce ω-hydroxy fatty acids, i.e., an omega hydroxy fatty acid. The EC number describing the biochemical reaction that converts a fatty acid into a ω-hydroxy fatty acid is EC 1.14.15.3. We provide non-limiting examples of suitable enzymes by their name and in parentheses provide an illustrative organism from which to source the genetic material, followed by fatty acid chain length specificity where C3-C10 indicates activity on fatty acids ranging in chain length from three to ten carbons, e.g. "Enzyme Name" ("Source Organism"; Chain length specificity). Any superscripts indicate references that describe the enzyme. Suitable enzymes for performing omega hydroxylation are as follows: P450alk1 (*C. Tropicalis*; C12-C16)[2,9,10]; CPR (*C. tropicalis*)[2]; P450 (3P2) (chimeric enzyme; C6-C12)[11]; P450 (pHP3) (Rabbit; C6-C12)[11]; P450 (*P. oleovarans*; C8-C12); P450 BM3 (*B. megaterium*; C12-C18); CYP86A8 (*A. thaliana*; C12-C18); CYP703A1 (*Petunia x hybrida*; C12) CYP704B2 (*O. sativa* ssp *japonica*; C18); CYP4V2 (*H. sapiens*; C12-C16); CYP4B (*H. sapiens*; C7-C10)[12]; CYP4A (*H. sapiens*; C10-C16)[12]; and CYP4F (*H. sapiens*; C16-C26)[12]. Although here and in all embodiments for α,ω-dicarboxylic acid production we employ an omega hydroxylase, in some embodiments hydroxylating other carbons within the fatty acid or diacid backbone may be useful and can be accomplished by hydroxylases in general. In one embodiment, a P450 BM3 that has an F87A mutation is used to change the regiospecificity of hydroxylation and demonstrates hydroxylation at the ω-1, ω-2, and ω-3 positions.

It will be readily apparent to those of skill in the art in view of this disclosure that ω-hydroxyfatty acids, i.e., 1-hydroxyfatty acids, are themselves valuable and used in the production of rapidly drying paints and varnishes, etc. As such, if of interest, the ω-hydroxyfatty acids, i.e., 1-hydroxyfatty acids, can be isolated or recovered in accordance with the invention.

The ω-hydroxyfatty acids, i.e., ω-hydroxyfatty acids, can be, in other embodiments, further oxidized to an α,ω-diacarboxylic acid. This omega hydroxy fatty acid can be further oxidized in accordance with the invention to a diacid using methods described herein. We provide fatty alcohol oxidases (FAOs) or fatty aldehyde dehydrogenases (FADs) to convert an omega-hydroxy fatty acid into an omega-oxo fatty acid in accordance with the biochemical reaction EC 1.1.3.20. In one embodiment, the fatty alcohol oxidase provided is FAO1, FAO2a or FAO2b from *Candida tropicalis*. In one embodiment, the route of oxidation is through an aldehyde using a FAO.

The aldehyde intermediate is then converted, in accordance with the invention, into a diacid by an aldehyde dehydrogenase (ALD). In general, many ALDs exist. The following are non-limiting examples of suitable enzymes by enzyme name and in parentheses, an illustrative source organism for the enzyme, and any associated specificity as a carbon chain length range (e.g., C4-C14): Ald1 (*Acinetobacter* sp M1; C4-C14); ScAld1 (*Mus musculus*; C6-C9); Psdr1 (*Homo sapiens*; C2-C12); ALD1, ALD2, ALD3, ALD4, ALD5, ALD6, HFD1 (*S. cerevisiae*; C2-C12).

Most cells naturally have the capacity to degrade fatty acids, hydroxyl fatty acids and diacids to some capacity through enzymatic activities associated with the β-oxidation pathway. Briefly, the pathway functions in most cases by activating free fatty acid groups to CoA thioesters with acyl-CoA ligases, which are further oxidized and degraded, proceeding through a 2,3 enoyl-CoA, 3-hydroxyacyl-CoA, 3-ketoacyl-CoA, and then to a two carbon-shortened acyl-CoA that repeats the cycle. The enzymatic activity required for this degradation is known. In accordance with the methods of this invention, we provide cells that have reduced or eliminated degradation pathways for fatty acids, hydroxyl fatty acids, and diacids compared to their wildtype counterparts. In some embodiments, the host organism is engineered in accordance with the invention to remove or attenuate genes encoding fatty acyl-CoA synthetase enzymes. In other embodiments, the host organism is engineered to remove or attenuate genes encoding acyl-CoA dehydrogenases. Methods for making host cells that are substantially β-oxidation pathway blocked are known to those of skill in the art. Here, and in accordance with the methods of the invention, we provide without limitation illustrative enzymes involved in fatty acid degradation that are removed or attenuated to increase fatty acid, hydroxyl fatty acid, or diacid production in an engineered host. In detail, we provide the enzyme name and in parantheticals its function. Superscripts provide references for certain enzymes. We provide host cells with the following enzymes removed or attenuated in *S. cerevisiae* or related yeasts that increase fatty acid, diacid or hydroxyl fatty acid production: ANT1 (adenine nucleotide transporter); POX2 (3 hydroxyacyl-CoA dehydrogenase); IDP3 (isocitrate dehydrogenase); POX1 (acyl-CoA oxidase); FOX3 (oxoacyl thiolase); EHD3 (hydrolase); PAST and PAS2 (peroxisomal formation protein); FAA1, FAA2, FAA3, and FAA4 (acyl-CoA synthetase). We provide host cells with the following enzymes removed or attenuated in *E. coli*: FadD and FadK (acyl-CoA synthetase); FadE and YdiO (acyl-CoA dehydrogenase); FadB, FadJ, and PaaZ (enoyl-CoA hydratase/hydroxyacyl dehydrogenase); FadA (3-ketoacyl thiolase); FadI (acetyl-CoA acyltransferase). We provide host cells with the following enzymes removed or attenuated in *B. subtilis* or related yeasts that increase fatty acid, diacarboxylic acid or hydroxy fatty acid production: YhfT, YhfL, LcfA, YdaB, YtcL, and BioW (acyl-coA synthetase); YdbM, YngJ, mmgC, acdA, and FadE (acyl-CoA dehydrogenase); YngF, YsiB, YhaR, and fadN (enoyl-CoA hydratase).

In addition, the host cell is, in some embodiments of the invention, genetically modified so that it has decreased or lacks expression of one or more genes encoding proteins involved in the storage and/or metabolism of fatty acid compounds, such that the storage and/or metabolism of fatty acid compounds by the host cell is decreased. Such genes include the following: the ARE1, ARE2, DGA1, and LRO1 genes. Other engineered host cells with genes that are modified are provided in accordance with the methods of the invention and include those set forth in Table IV. The "enzyme" column provides the name of the enzyme to be modified; the "manipulation" column provides the modification to the enzyme that is provided and is either "attenuate" or "OE". Here attenuate means either decreasing the enzyme activity or completely eliminating it; "OE"=overexpress. The superscripts refer to references.

TABLE IV

Genes Involved in Storage/Metabolism of FA Compounds

| Enzyme | Manipulation | Organism |
| --- | --- | --- |
| SNF2 | attenuate | S. cerevisiae[16] |
| IRA2 | attenuate | S. cerevisiae[16] |
| PRE9 | attenuate | S. cerevisiae[16] |
| PHO90 | attenuate | S. cerevisiae[16] |
| SPT21 | attenuate | S. cerevisiae[16] |
| ARE1 | attenuate | S. cerevisiae[17] |
| ARE2 | attenuate | S. cerevisiae[17] |
| DGA1 | attenuate | S. cerevisiae[17] |
| LRO1 | attenuate | S. cerevisiae[17] |
| ACL1 | OE | A. nidulans |
| ALD6 | OE | S. cerevisiae |
| ACS1 | OE | S. enterica |
| MAE1 | OE | S. cerevisiae |
| GLC3 | attenuate | S. cerevisiae |
| GLG1, GLG2 | attenuate | S. cerevisiae |

In general, cells do not naturally biosynthesize odd-chain alpha, α,ω-dicarboxylic acids. However, an odd-chain α,ω-dicarboxylic acid does appear in biotin biosynthetic pathways usually as a bound intermediate to the acyl carrier protein of fatty acid biosynthesis. Biotin biosynthesis is found in some, but not all organisms, which are therefore auxotrophic for biotin. The bound intermediate is the C7 α,ω-dicarboxylic acid, pimelic acid, which is always bound as a pimeloyl-ACP until it is condensed with alanine where it is sequestered into the production of biotin. Until recently, the precise mechanism of pimeloyl-ACP formation has remained elusive. Now E. coli's pathway to this intermediate has been reported to proceed by methylating malonyl-CoA with a methyltransferase, BioC, followed by condensation with malonyl-ACP to form 3-oxo-glutaryl-ACP methyl ester by fabH, followed by two full reduction-dehydration cycles and one extension by the fatty acid synthases (fabG, fabZ, fabI, fabB). The methyl ester is then converted into the free ω-carboxylic acid, pimeloyl-ACP by activity conferred by bioH (see Lin S, et al. Nature Chemical Biology 6, 682-688 (2010)). A different pathway for biotin biosynthesis in B. subtilis has been suggested to employ a P450 (BioI, CYP107H1) that in vitro is reported to cleave a carbon-carbon bond in a C14 fatty acyl-ACP to form two C7 molecules (see, e.g., Cryle, et al., "Structural insights from a P450 Carrier Protein complex reveal how specificity is achieved in the P450(BioI) ACP complex," Proc Natl Acad Sci USA 105, 15696-701 (2008); and Cryle et al., "Products of cytochrome P450(BioI) (CYP107H1)-catalyzed oxidation of fatty acids," Org Lett 5, 3341-4 (2003), the teachings of both of which are incorporated by reference). Yet, this work remains unclear and no one has identified free pimelic acid from B. subtilis cultures, potentially due to the very low levels of biotin required to support cell growth.

In accordance with the methods of this invention, we provide engineered host cells capable of producing odd-chain ω-hydroxyl fatty acids and α,ω-dicarboxylic acids in three general strategies that employ hybrid Type I PKSs, engineered portions of the B. subtilis biotin pathway, or engineered portions of the E. coli biotin pathway in a variety of embodiments.

In one embodiment, a hybrid PKS system is used to produce heptanedioic (pimelic) acid, which is then oxidized with the methods described above. In one embodiment, a hybrid PKS is constructed and is composed of a loading module for either propionyl-CoA or methylmalonyl-CoA such that the starting unit is odd-chain. While there exist numerous loading modules that perform this function, one suitable loading module is selected from the Erythromycin PKS to load propionyl-CoA. This loading module is operatively linked to two extension-condensation modules that condense malonyl-CoA into the growing acyl-ACP chain. One suitable choice for these modules is the Nystatin PKS M5 and M15. Finally, the hybrid PKS is terminated with a thioesterase that cleaves the thioester bond and releases heptanoic acid. One suitable choice for the thioesterase is that from the Erythromycin PKS (DEBS TE). This construct is cloned into an expression vector and transformed into cells that have phosphopantetheinylation activity to activate the hybrid PKS, the cells are grown in appropriate medium and the free fatty acid heptanoic acid is produced. In some embodiments, the cells co-express the hybrid PKS and a set of enzymes for omega hydroxylation as described previously to further oxidize heptanoic acid into pimelic acid. In some embodiments the cells have no detectable levels of pimelic acid or do not have any known pathways for its production. In some embodiments the cells are C. tropicalis, B. subtilis, E. coli or S. cerevisiae.

In another embodiment, pimelic acid is produced by engineering a B. subtilis host. Specifically, engineered cells are provided that overexpress the gene encoding P450 BioI (bioI) and higher levels of pimelic acid are detected (compared to wild-type). The enzyme cleaves the central carbon-carbon bond in a C14 fatty acyl-ACP by consecutive formation of alcohol and threo-diol intermediates to form pimelate. In one embodiment, BioI is overexpressed by cloning it behind a regulatable promoter for expression in B. subtilis and includes Pctc, PgsiB and results in pimelic acid production. In other embodiments, BioI is overexpressed by cloning it behind constitutive promoters derived from the sigma A or sigma B RNA polymerase promoter sequence. Additionally, biotin itself is a valuable chemical derived from pimelate, so overproduction of pimelate in accordance with the methods and host cells of the invention decreases the costs of microbial biotin production. In another embodiment, a thioesterase is expressed to increase the pimelate production. In another embodiment, the fatty acid synthesis enzymes native to B. subtilis are overexpressed which results in increased pimelate production. Suitable enzymes are provided in Table I.

In another embodiment, P450 bioI is overexpressed in E. coli, a non-native organism, with or without overexpression of the B. subtilis fatty acid enzymes (acpP, accABCD, KS, KR, ER, DH). In some embodiments, expression of a thioesterase is employed to increase release of the pimelate from the ACP. In another embodiment, the P450 BioI is overexpressed in S. cerevisiae with or without the B. subtilis fatty acid enzymes (KS, KR, ER, DH, acpP) and a thioesterase and pimelate is produced.

In another embodiment, fatty acid biosynthetic genes are expressed from D. vulgaris or D. deslfuricans including the 3-oxoacyl acyl carrier protein reductase (fabG) (Accession No. YP_011773.1), the acpP (Accession No. YP_011774.1), the beta ketoacyl ACP synthase (fabF) (Accession No. YP_011775.1), the beta-hydroxyacyl ACP dehydratase (FabA/Z like) (Accession No. YP_011772.1) and pimelate is produced. In some embodiments, additional expression of the NC_002937 gene or thioesterase supports pimelate biosynthesis as an auxiliary protein based upon close proximity within the natural D. vulgaris gene cluster.

In another embodiment, *E. coli* genes are expressed in the native host or a heterologous host to produce pimeloyl-ACP and include bioC, fabF, fabG, fabA/Z, and fabI. In order to remove the methyl ester bonded to the omega carboxylate, some embodiments include the expression/overexpression of bioH. Once the omega carboxylate is exposed a fatty acid synthase editing TE releases the pimelic acid from the acp-thioester. This TE is naturally produced or can be overexpressed to increase pimelic acid production. However, in some cases the pimelate methyl ester is desired. In some embodiments, expression of a thioesterase increases the production of pimelate or methyl pimelate. In another embodiment, the genes required for pimelic acid production in *E. coli* are expressed in *S. cerevisiae* and result in production of pimelic acid.

The enzymes described herein can be readily replaced using a homologous enzyme thereof A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which do not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

Nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. Further, nucleic acid sequences for use in the invention can be obtained from commercial vendors that provide de novo synthesis of the nucleic acids.

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host cell simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon and followed by a terminator in the case of *E. coli* or other prokaryotic hosts. See Shine et al. (1975) *Nature* 254:34 and Steitz, in Biological Regulation and Development: Gene Expression (ed. R. F. Goldberger), vol. 1, p. 349, 1979, Plenum Publishing, N.Y. In the case of eukaryotic hosts like yeast a typical expression vector contains the desired nucleic acid sequence preceded by one or more regulatory regions, along with a Kozak sequence to initiate translation and followed by a terminator. See Kozak M (1984). *Nature* 308 (5956): 241-246.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples for prokaryotic expression include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA*, 80:21-25.). Examples of promoters to use for eukaryotic expression include pTDH3, pTEF1, pTEF2, pRNR2, pRPL18B, pREV1, pGAL1, pGAL10, pGAPDH, pCUP1, pMET3, pPGK1, pPYK1, pHXT7, pPDC1, pFBA1, pTDH2, pPGI1, pPDC1, pTPI1, pENO2, pADH1, and pADH2. As will be appreciated by those of ordinary skill in the art, these and other expression vectors or elements may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19, pRS series; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell. In addition to the use of expression vectors, strains are built where expression cassettes are directly integrated into the host genome.

The expression vectors or integration cassettes of the invention must be introduced or transferred into the host cell. Such methods for transferring the expression vectors into host cells are well known to those of ordinary skill in the art. For example, one method for transforming E. coli with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain a carbon source, such as a sugar (e.g., glucose) when an intermediate is not introduced. In this way, cellular production of acetyl-CoA, the starting material for the production of the diacids, is ensured. When added, the intermediate is present in an excess amount in the culture medium or cells.

As the host cell grows and/or multiplies, expression of the enzymes necessary for producing the fatty acid, hydroxyl fatty acid, 1-oxo fatty acid, 1-ol fatty acid and the diacid is effected. Once expressed, the enzymes catalyze the steps necessary for carrying out the enzymatic steps shown in FIGS. 1 and 4. If an intermediate has been introduced, the expressed enzymes catalyze those steps necessary to convert the intermediate into the respective fatty acid derived compounds. Any means for recovering the diacid from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC).

Host Cells

The host cells of the present invention are genetically modified in that heterologous nucleic acid have been introduced into the host cells or naturally occurring cells have been engineered to produce higher levels of a given product, and as such the genetically modified host cells do not occur in nature. The suitable host cell is one capable of expressing a nucleic acid construct encoding an enzyme capable of catalyzing a desired biosynthetic reaction in order to produce the enzyme for producing the desired fatty acid or fatty acid derived molecule. Such enzymes are described herein. In some embodiments, the host cell naturally produces some of the precursors, as shown in FIGS. 1 and 4, for the production of the fatty acid derived compounds. These genes encoding the desired enzymes may be heterologous to the host cell or these genes may be native to the host cell but are operatively linked to heterologous promoters and/or control regions, which result in the higher expression of the gene(s) in the host cell. In other embodiments, the host cell does not naturally produce the fatty acid starting material and comprises heterologous nucleic acid constructs capable of expressing one or more genes necessary for producing the fatty acid.

Each of the desired enzymes capable of catalyzing the desired reaction can be native or heterologous to the host cell. Where the enzyme is native to the host cell, the host cell is optionally genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

The genetically modified host cell can further comprise a genetic modification whereby the host cell is modified by the increased expression of one or more genes involved in the production of fatty acid compounds from one of five methods provided such that the production of fatty acid compounds by the host cell is increased. Such genes encode enzymes related to either Type I, II, or III fatty acid biosynthesis, hybrid Type I polyketide synthesis, or 2-ketoacid biosynthesis and include: acetyl carboxylase (ACC), ketosynthase, ketoreductase, deyhdratase, enoyl reductase, cytosolic thioesterase ('TesA, sometimes referred to as LTesA), and acyl-carrier protein (AcpP). In some embodiments, the genetically modified host cell is modified to produce higher levels of cytosolic acetyl-coA or malonyl-CoA or the pathway may be targeted to the mitochondria or compartment where there is a natural or engineered abundance of acetyl-CoA and other necessary precursors. Thus, in some embodiments, a host cell of the invention comprises a modification to express, or increase expression of a protein such as ATP citrate lyase, and to increase levels of NADPH, malic enzyme. For example, Saccharomyces cerevisiae has little ATP citrate lyase and can be engineered in accordance with the invention to express ATP citrate lyase by introducing an expression vector encoding ATP citrate lyase into the yeast cells.

In some embodiments, a genetically modified host cell is modified to increase expression of a Type I (prokaryotic, eukaryotic) or Type II (prokaryotic) or Type III fatty acid synthase (FAS) gene or Type I polyketide synthase (PKS) or 2-ketoacid biosynthetic enzymes. For example, a yeast host cell is modified to express a FAS gene. Fatty acid synthase proteins are known in the art. FAS3 catalyzes the first committed step in fatty acid biosynthesis and in yeast is encoded by a 6.7 kb gene and contains two enzymatic domains: biotin carboxylase, and biotin carboxyltransferase. FAS2 is encoded, in yeast, by a 5.7 kb gene and contains four domains: an acyl-carrier protein, beta-ketoacyl reductase, beta-ketoacyl synthase, and phosphopantetheinyl transferase (PPT). FAS1 is encoded, in yeast, by a 6.2 kb gene and contains five domains: acetyltransacylase, dehydratase, enoyl reductase, malonyl transacylase, and palmitoyl transacylase. FAS1 and FAS2 complex to form a heterododecamer, containing six each of FAS1 and FAS2 subunits (Lomakin et al., *Cell* 129:319-322, 2007, incorporated herein by reference). In some embodiments, a genetically modified host cell overexpresses or expresses native and/or non-native type II fatty acid synthase enzymes. Illustrative genes that encode the enzymes are provided: acpP, accA, accB, accC, accD, fabD, fabH, fabG, fabZ, fabA, fabI, fabB, fabF, fadR. In some embodiments a genetically modified host cell overexpresses or expresses hybrid engineered type I polyketide synthases.

The genetically modified host cell can further comprise a genetic modification whereby the host cell is modified by the decreased or lack of expression of one or more genes encoding proteins involved in the storage and/or metabolism of fatty acid compounds; such that the storage and/or metabolism of fatty acid compounds by the host cell is decreased. Such genes include the following: the ARE1, ARE2, DGA1, and/or LRO1 genes. In some embodiments, the host cell is modified by the decreased or lack of expression of genes that are involved in the β-oxidation of fatty acids. For example, in yeast such, e.g., *Saccharomyces cerevisiae*, β-oxidation occurs in the peroxisome. Genes such as PAT1 and PEX11 are peroxisomal proteins involved in degradation of long-chain and medium-chain fatty acids, respectively. Accordingly, a host cell may be modified in accordance with the invention to delete PAT1 and/or PEX11, or otherwise decrease expression of the PAT1 and/or PEX11 proteins.

The genetically modified host cell of the invention can further comprise a genetic modification whereby the host cell is modified to express or have increased expression of an ABC transporter that is capable of exporting or increasing the export of any of the fatty acid derived compounds from the host cell. Such an ABC transporter is the plant cer5 or dcuC.

The present invention provides a wide variety of prokaryotic or eukaryotic host cell suitable for use in the present method and methods for making such host cells. In some embodiments, the bacteria is a cyanobacteria. Examples of suitable bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis,* and *Paracoccus* taxonomical classes.

Suitable eukaryotic cells include, but are not limited to, fungal, insect or mammalian cells. Suitable fungal cells are yeast cells, such as yeast cells of the *Saccharomyces* genus. In some embodiments the eukaryotic cell is an algae, e.g., *Chlamydomonas reinhardtii, Scenedesmus obliquus, Chlorella vulgaris* or *Dunaliella salina*.

In some embodiments, the host organism is yeast. Suitable yeast host cells include, but are not limited to, *Yarrowia, Candida, Bebaromyces, Saccharomyces, Schizosaccharomyces* and *Pichia*. In one embodiment, the yeast host cell is a species of *Candida* selected from the group consisting of *C. tropicalis, C. maltosa, C. apicola, C. paratropicalis, C. albicans, C. cloacae, C. guillermondii, C. intermedia, C. lipolytica, C. panapsilosis* and *C. zeylenoides*. In one embodiment, *Candida tropicalis* is employed as the host organism.

The present invention provides for an isolated fatty acid derived compound produced by the method of the present invention. Isolating the fatty acid derived compound involves the separating at least part or all of the fermentation medium, host cells, and parts thereof, from which the fatty acid derived compound was produced, from the isolated fatty acid derived compound. The isolated fatty acid derived compound may be free or essentially free of impurities formed from at least part or all of the host cells, and parts thereof. The isolated fatty acid derived compound is essentially free of these impurities when the amount and properties of the impurities do not interfere in the subsequent use of the fatty acid derived compound. For example, if the subsequent use is as an industrial chemical, such as a chemical to be used in a polymerization reaction, then the compound is essentially free of impurities when any remaining impurities would not interfere with the use of the compound as an industrial chemical in a polymerization reaction or any other downstream industrial reaction. If the product is to be used as a fuel, such as a fuel to be used in a combustion reaction, then the compound is essentially free of impurities when any impurities remaining would not interfere with the use of the material as a fuel. In some instances, the host cells of the invention do not naturally produce the desired fatty acid derived compound.

The fatty acid derived compound of the present invention are useful not only as fuels as a chemical source of energy but also as industrial chemicals and precursors thereof that can be used as an alternative to petroleum derived fuels, ethanol and the like, and industrial chemicals and their precursors. The fatty acid derived compounds of the present invention are also useful in the synthesis of alkanes, alcohols, and esters of various for use as a renewable fuel or for industrial chemical production. In addition, the fatty acid derived compounds can also be as precursors in the synthesis of therapeutics, high-value oils, such as a cocoa butter equivalent and animal feeds. The fatty acid derived compounds are also useful in the production of the class of eicosanoids or related molecules, which have therapeutic related applications.

It is to be understood that, while the invention is described herein in conjunction with specific embodiments thereof, the foregoing description is intended to illustrate and not limit the scope of the invention. Other aspects, advantages, and modifications within the scope of the invention will be apparent to those skilled in the art to which the invention pertains in view of this disclosure.

All patents, patent applications, and publications mentioned herein are hereby incorporated by reference in their entireties.

The invention having been described, the following examples are offered to illustrate the subject invention by way of illustration, not by way of limitation.

EXAMPLES

Example 1

Production of Tetradecanedioic Acid

In accordance with various embodiments of the present invention, tetradecanedioic acid is produced. In one embodiment, a heterologous type III fatty acid synthase ELO1 and ELO2 (*T. brucei*) are expressed in conjunction with a set of enzymes that encode for the production of butyryl-CoA, which in some embodiments include phaA, phaB, phaJ, ter, and a thioesterase, which in some embodiments are encoded by ltesA to produce tetradecanoic acid. The tetradecanoic acid is then converted through the alcohol and aldehyde intermediate into the diacid tetradecanedioic acid by expressing a P450 and FAO.

In another embodiment, a native type II FAS system and a thioesterase from *E. coli* that produces tetradecanoate were expressed in a host cell of the invention. Once produced, the tetradecanoate is further oxidized in accordance with the invention at the omega carbon by P450s. Although many thioesterases are suitable for these embodiments, in one embodiment the 1TesA from *E. coli* is employed. Although many P450s or omega oxidases are suitable for these embodiments, in one embodiment the P450 BM3 from *B. subtilis* is employed. Briefly, P450 BM3 and a mutant P450 BM3 (F87A) were separately cloned using standard methods and inserted behind the TAC promoter on an *E. coli* expression plasmid that contained the p15a origin of replication, and an ampicillin resistant gene. A thioesterase, 1TesA was cloned using standard methods and inserted behind the LacUV5 promoter on an *E. coli* expression plasmid that contained the pBBR origin of replication and a tetracycline resistance gene. Plasmid maps are included in FIG. 3. The host cells harboring expression plasmids for the LtesA and p450 BM3 or LtesA and p450 BM3 (F87A) were grown in LB media at 37 degrees C. and induced at OD=0.5 with 1 mM IPTG. Cells were grown for 48 h and separated from the supernatant by centrifugation. Both supernatant and pellet fraction were separately dried and resuspended in MeOH:H20 (1:1 v/v). Chemical standards were purchased from Sigma and were made up to 20 μM, in methanol and water (1:1, v/v). The separation of diacids was conducted on a ZIC-HILIC column (250 mm length, 2.1 mm internal diameter, and 3.5 μm particle size; from Merck SeQuant, and distributed via The Nest Group, Inc., MA., USA) using an Agilent Technologies 1200 Series HPLC system (Agilent Technologies, CA, USA). An injection volume of 4 μL was used throughout. The auto-sample tray was maintained at 4° C. by an Agilent FC/ALS Thermostat. The column compartment was set to 50° C. Analytes were eluted isocratically with a mobile phase composition of 50 mM ammonium acetate, in water, and acetonitrile (3.6:6.4, v/v). A flow rate of 0.1 mL/min was used throughout.

The HPLC system was coupled to an Agilent Technologies 6210 time-of-flight mass spectrometer (LC-TOF MS), by a ⅓ post-column split. Contact between both instrument set-ups was established by a LAN card to trigger the MS into operation upon the initiation of a run cycle from the MassHunter workstation (Agilent Technologies, CA, USA). Electrospray ionization (ESI) was conducted in the negative ion mode and a capillary voltage of −3500 V was utilized. MS experiments were carried out in full scan mode, at 0.85 spectra/second and a cycle time of 1.176 seconds, for the detection of [M-H]-ions. The instrument was tuned for a range of 50-1700 m/z. Prior to LC-TOF MS analysis, the TOF MS was calibrated via an ESI-L-low concentration tuning mix (Agilent Technologies, CA, USA). Data acquisition and processing were performed by the MassHunter software package (Agilent Technologies, CA, USA).

Figure 2A:
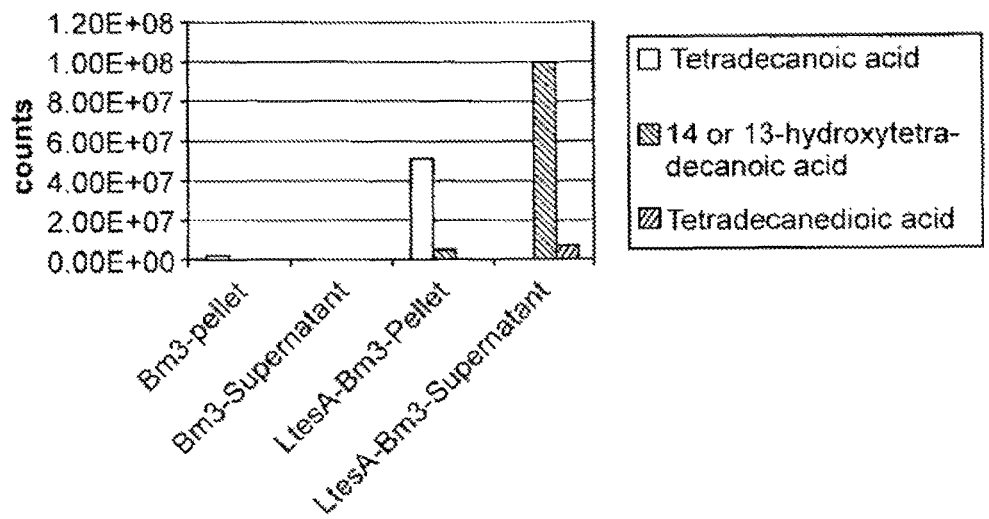
FIGS. 2A and 2B illustrate FT-MS analysis of strains producing diacids from co-cultures expressing LtesA and one of two P450s. Strain BM3 is an engineered *E. coli* host DH1 ΔfadD expressing P450-Bm3 and P450-Bm3 (F87A); strain LtesA-Bm3 is an engineered *E. coli* host DH1 ΔfadD expressing LtesA, P450-Bm3, and P450-Bm3 (F87A). Strains were analyzed for production of fatty acid, ω-hydroxyacid, and the α,ω-dicarboxylic acid. (See, Example 1 below).
Figure 2B:
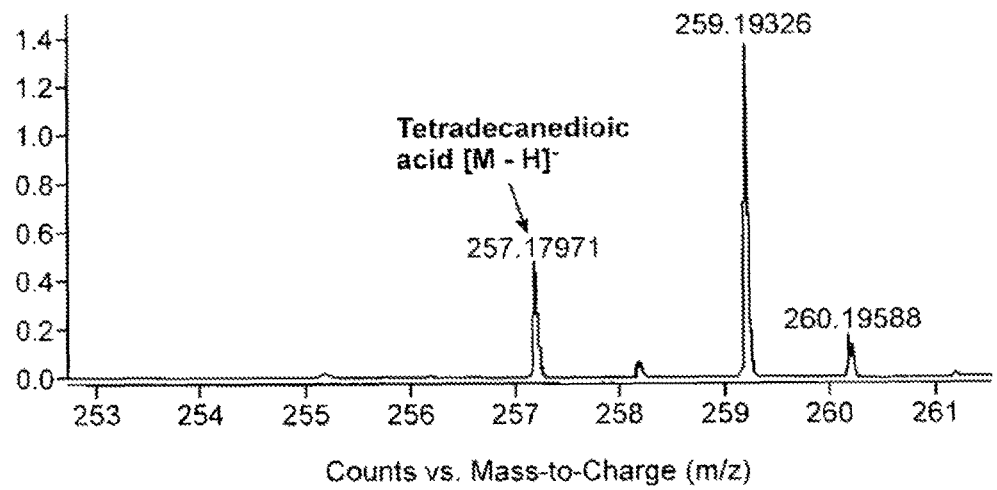
Figure 3:
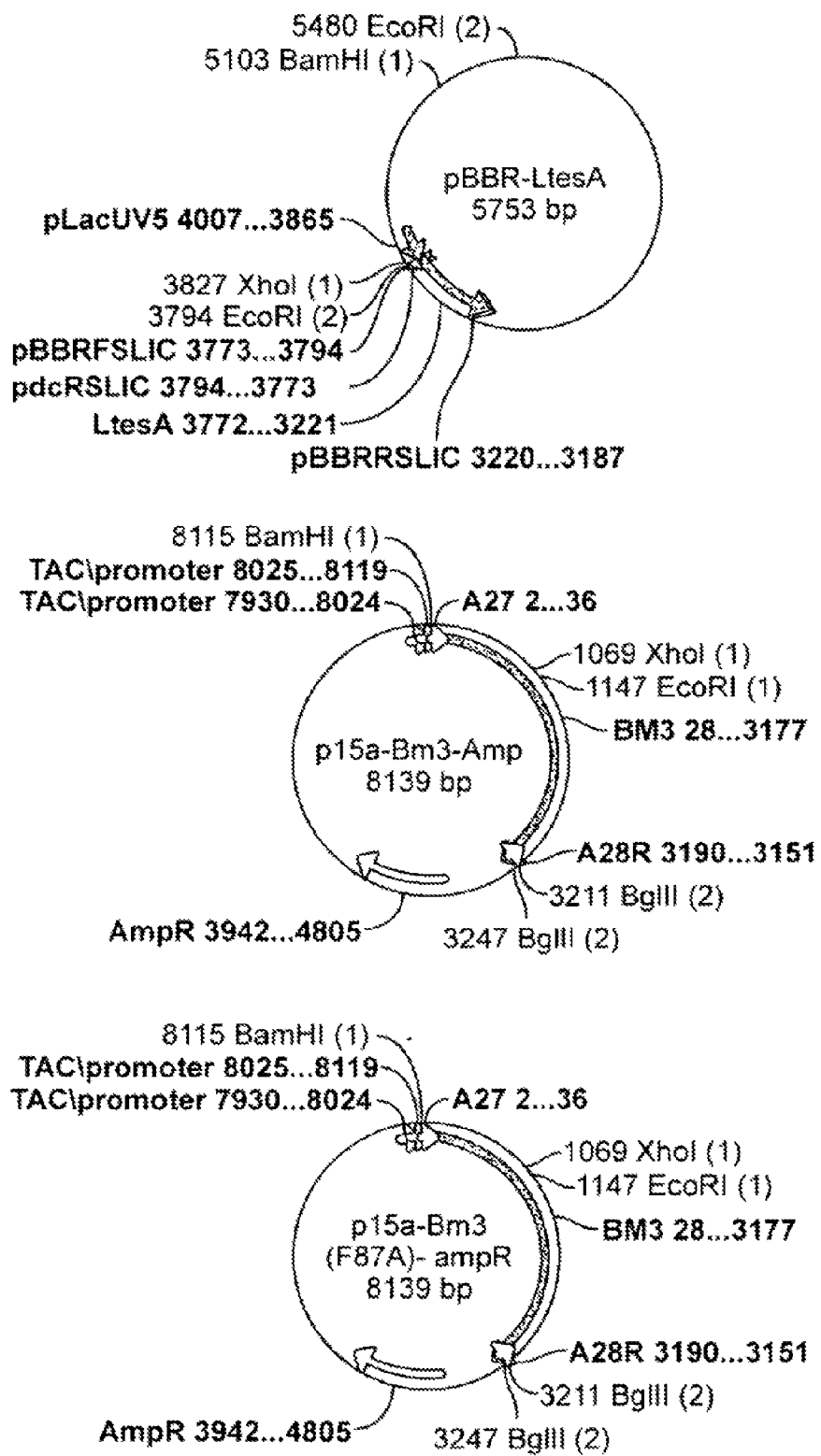
FIG. 3 illustrates the plasmids that were used in Example 1, below. *E. coli* DH1 ΔfadD was employed; cultures were grown for 24 h in TB media with 1 mM IPTG at 30° C., sampled, and analyzed for production of fatty acid, ω-hydroxyacid, and the α,ω-dicarboxylic acid.

FIGS. 2 and 3 illustrate that the expression of both the wild-type P450 Bm3 and the engineered P450 BM3 (F87A) resulted in diacid production when the native *E. coli* fatty acid pathway is overexpressed via LtesA. Data shown in FIG. 2 demonstrated production and excretion of the C14 α,ω-dicarboxylic acid tetradecanoate. Specifically, FIG. 2A demonstrated production of both the C14 ω-hydroxytetradecanoic acid and tetradecanedioic acid. FIG. 2B is MS data that show the expected molecular ion of tetradecanedioic acid.

Example 2

Production of Butanedioic Acid

In accordance with the methods of the invention, butanedioic is produced by a variety of embodiments. This example describes converting acetyl-CoA into butyryl-CoA, which is cleaved from the CoA by a thioesterase (TES), oxidized by a P450 monooxygenase (OX1) and further oxidized into its respective diacid by another oxidase (OX2). Importantly, a thioesterase can be engineered in accordance with the invention so that it cleaves hydroxybutyrate from its CoA, allowing for the production of 2-hydroxybutanedioic acid.

The above method is merely illustrative of the many embodiments provided by the invention. Another embodiment involves the use of a PKS composed of a loading module that incorporates malonyl-CoA an extension module and a TE that releases a butyrate product. In this embodiment, the fatty acid is then oxidized into omega hydroxybutyrate and finally into butanedioic acid. While many PKS modules can be used, in one embodiment, a malonyl-CoA loading module from the niddamycin PKS is functionally attached to an extension and full reduction module from the nystatin PKS (module 5) to provide a PKS of the invention. To release the product as a fatty acid, a TE, for example, the DEBS PKS TE, is functionally attached to the nystatin module. This sequence is placed into an expression vector for *E. coli*, expressed at 15C-37 degrees C. and results in production of butyric acid (SEQ ID NO:1 below). Additional expression of a short chain oxidase (OX1 and OX2) further results in production of butanedioic acid in accordance with the invention.

Example 3

Production of Hexanedioic Acid

In accordance with various embodiments of the methods of the invention, hexanedioic acid is produced. In one embodiment, genes in the aflatoxin biosynthesis pathway that encode fatty acid biosynthesis reactions resulting in a final C6 fatty acid product, hexAB are used. Because others have reported that the hexanoic acid is bound to the hexAB enzyme[3], in some embodiments, the hexAB has been mutated to decrease or eliminate such binding, and in other embodiments, a thioesterase (TES) is expressed that cleaves the C6 fatty acid from its thioester. In another embodiment, the transacylase from the PKS is used to load an ACP and subsequently cleave it with a TES. In another alternative embodiment, a short-chain thioesterase is engineered to directly produce the C6 fatty acid from type II fatty acid biosynthesis (see, e.g, Dehesh, et al., "Production of high levels of 8:0 and 10:0 fatty acids in transgenic canola by overexpression of Ch FatB2, a thioesterase cDNA from *Cuphea hookeriana.*" *Plant J* 9, 167-72 (1996)). Once produced, the hexanoate is further oxidized in accordance with the invention at the omega carbon by P450s. Although many P450s or omega oxidases are suitable for these embodiments, in one embodiment the P450 BM3 from *B. subtilis* is employed, either native or engineered. In various embodiments, additional expression of a P450 monoxygenase and reductase (P4503P2 and CPR) further results in production of adipate, in accordance with the invention.
Scheme II The above embodiments are merely illustrative. Another embodiment utilizes an engineered PKS of the invention composed of a loading module that incorporates malonyl-CoA, two extension modules, and a TE that releases a final hexanoate product. This fatty acid is then oxidized into omega hydroxybutyrate and finally into hexanedioic acid (adipate) by, in one embodiment, expression of P4503P2, CPR, and a FAO/ALD in the host cell. More specifically, a malonyl-CoA loading module from the niddamycin PKS is functionally attached to an extension and full reduction module from the nystatin PKS (module 5), followed by another extension and full reduction module from the nystatin PKS (module 15) to provide a PKS of the invention. To release the product as a fatty acid, a TE, optionally the DEBS PKS TE, is functionally attached to the last nystatin module. This sequence is placed into an expression vector for *E. coli*, expressed at 15-37 degrees C., resulting in production of hexanoic acid (sequence hex orf 1 & hex orf 2, i.e, SEQ ID NOS:2 and 3, respectively, below). Additional expression of a short chain oxidase (OX1 and OX2) in accordance with the invention further results in production of adipic acid.

Example 4

Production of Octanedioic Acid

In accordance with various embodiments of the present invention, octanedioic acid is produced. In one embodiment, engineered host cells are provided that express a native type II FAS system and a heterologous thioesterase, ChFatB2 from *C. hookeriana* to produce octanoate. The octanoate is further converted into the diacid octanedioic acid by expression of a hydroxylase (P4503P2) and an FAO/FAD, ADH combination.
Scheme III Example 5

Production of Decanedioic Acid

In accordance with various embodiments of the present invention, decanedioic acid is produced. The thioesterase, ChFatB2, from *C. hookeriana*, produces decanoate. In one embodiment, host cells are modified to produce decanedioic acid by expressing a native type II FAS system and a thioesterase, ChFatB2 from *C. hookeriana*, to produce decanoate. In another embodiment host cells are modified to produce decanedioic acid by expressing a type III fatty acid synthase, ELO1 (*T. brucei*) and has appropriate genes for the production of butyryl-CoA, which in some embodiments include phaA, phaB, phaJ, ter, and a thioesterase, which in some embodiments are encoded by ChFatB2. Although many P450s could be employed, in one embodiment, the decanoate is then converted in accordance with the invention into the diacid decanedioic acid by expressing P4503P2 and FAO/FAD, ADH combination.
Scheme IV Example 6

Production of Dodecanedioic Acid

In accordance with various embodiments of the present invention, dodecanedioic acid is produced. In one embodiment, a host cell containing a native type II FAS system and a heterologous thioesterase, UcFATB1 from *U. californica* that produces dodecanoate, is provided. The dodecanoate can be further oxidized in accordance with the invention at the omega carbon by P450s.
Scheme V Example 7

Production of C14(n+2) α,ω-Dicarboxylic Acids

The methods presented above can be used to produce of longer chain diacids up to C26 and longer, with longer chain fatty acid biosynthesis systems existing in organisms such as mycoplasms, etc.

Example 8

Engineering Thioesterase Substrate Specificity

Thioesterase substrate specificity can be engineered in accordance with the methods of the invention to produce specific fatty acid chain lengths (see, e.g., Yuan et al., *Proc Natl Acad Sci USA* 92, 10639-43 (1995); see also, references 4 and 6).

Example 9

Oxidation by P450 BM3

Terminal oxidation can be carried out by the wild-type P450 BM3 monoxygenase using an ω-hydroxyfatty acid as a substrate (see, e.g., Schneider et al., "Production of alkanedioic acids by cytochrome P450 BM3 monooxygenase: oxidation of 16-hydroxyhexadecanoic acid to hexadecane-1,16-dioic acid," *Biocataysis and Biotransformation,* 17:163-178 (1999)). Thus, in addition to the previous examples that utilize fatty alcohol oxidation/fatty alcohol dehydration and aldehyde dehydration, the final oxidation is, in some embodiments, carried out by the P450 BM3 enzyme. Further, the hydroxylation position can be changed to the ωcarbon by a point mutation, resulting in ω-hydroxylation of laurate (see, Oliver, et al., "A single mutation in cytochrome P450 BM3 changes substrate orientation in a catalytic intermediate and the regiospecificity of hydroxylation," *Biochemistry* 36, 1567-72 (1997)). Thus, expression of both the wild-type P450 BM3 and the engineered P450 BM3 (F87A) results in diacid production if fatty acids are supplied. Further, the substrate specificity can be changed to shorter chain length fatty acids by introduction of various point mutations, resulting in oxidation of short chain length substrates (see, Ost, et al. "Rational re-design of the substrate binding site of flavocytochrome P450 BM3." *FEBS Letters* 486, 173-177 (2000)).

Example 10

Controlling Saturation

Fatty acid saturation can be controlled by expressing desaturases or, alternatively, by overexpressing fadR.

Example 11

Controlling Internal Hydroxylation

Other P450s hydroxylate various ω-1,2,3 positions and produce long chain molecules that resemble polyhydroxy-alkanoates. Alternatively, one can cleave the thioester early in the fatty acid reduction/elongation cycle to produce molecules like 2-hydroxymyristate in accordance with embodiments of the invention.

Example 12

Biosynthetic Route to Omega Hydroxy Fatty Acids

Omega hydroxy fatty acids themselves are valuable as polymer substrates and can easily be produced with an embodiment of the invention in which example number 6 above is utilized after eliminating the FAO/FAD and ADH enzyme activities.

Example 13

Providing Fatty Acid Substrate Through Type I Fatty Acid Biosynthesis

Alternate methods of the invention utilize Type I fatty acid biosynthesis for controlling fatty acid chain length through short chain elongation systems. This results in production of specific acyl-CoA chain lengths ranging from C4, C10, C14, C18, C20, C22, and C26. The fatty acid substrates are cleaved from the CoA thioester by expressing a thioesterase that has broad substrate range. The fatty acid of desired chain length can then be omega oxidized to form its respective diacid, as described in Examples 1-6.

Example 14

Production of Odd Chain α,ω-Dicarboxylic Acids

Odd chain diacids are also valuable molecules that can be produced through decarbonylation of fatty acids to produce an odd chain fatty acids in accordance with the invention. This odd chain fatty acids are then oxidized utilizing the oxidation methods described herein. Alternatively, odd chain fatty acids are produced when propionyl-CoA is used as a primer for fatty acid or polyketide synthases (instead of acetyl-CoA). Once the odd chain fatty acids are produced via these methods, they proceed through omega oxidation as described above.

Example 15

Production of C7 Diacid (Pimelic Acid)

Pimelic acid is a precursor to the biotin biosynthesis pathway and is produced naturally in different organisms by different pathways relating to fatty acid like mechanisms. The present invention provides a variety of embodiments for the production of pimelic acid.

In one embodiment, the gene encoding native or engineered P450 BioI (bioI) native to *B. subtilis* is overexpressed in *B. subtilis* by cloning behind a sigma B RNA polymerase constitutive promoter and higher levels of pimelic acid are detected (compared to wild-type). The enzyme cleaves the central carbon-carbon bond in a C14 fatty acyl-ACP by consecutive formation of alcohol and threo-diol intermediates to form pimelate. Additionally, biotin itself is a valuable chemical derived from pimelate, so overproduction of pimelate in accordance with the methods and host cells of the invention decreases the costs of microbial biotin production.

In another embodiment, P450 bioI is overexpressed in *E. coli*, a non-native organism, with or without overexpression of the *B. subtilis* fatty acid enzymes (acpP, accABCD, KS, KR, ER, DH). In some embodiments, expression of a thioesterase is employed to increase release of the pimelate from the ACP.

In another embodiment, the P450 BioI is overexpressed in *S. cerevisiae* with or without the *B. subtilis* fatty acid enzymes (KS, KR, ER, DH).

In another embodiment, the orfs following bioI, ytbQ and ytcP and ytcQ (*B. subtilis*) are expressed to increase pimelate production. In another embodiment, a thioesterase is expressed to increase the pimelate production.

In another embodiment, a hybrid PKS system is used to produce heptanedioic acid which is then oxidized with the methods described above. Specifically, a PKS propionyl-CoA or methylmalonyl-CoA is functionally linked to two malonyl-CoA extension and reduction modules and finally to a TE module and expressed in *E. coli* to produce heptanoic acid. Expression of the omega oxidizing enzymes results in oxidation of the heptanoic acid to heptanedioic (pimelic) acid.

In another embodiment, fatty acid biosynthetic genes are expressed from *D. vulgaris* or *D. deslfuricans* including the 3-oxoacyl acyl carrier protein reductase (fabG) (Accession No. YP_011773.1), the acpP (Accession No. YP_011774.1), the beta ketoacyl ACP synthase (fabF) (Accession No. YP_011775.1), the beta-hydroxyacyl ACP dehydratase (FabA/Z like) (Accession No. YP_011772.1) to produce pimelate. In some embodiments, additional expression of the NC_002937 gene or thioesterase supports pimelate biosynthesis as an auxiliary protein based upon close proximity within the natural *D. vulgaris* gene cluster.

In another embodiment, *E. coli* genes are expressed in the native host or a heterologous host to produce pimeloyl-ACP and include bioC, fabF, fabG, fabA/Z, and fabI. In order to remove the methyl ester bonded to the omega carboxylate, some embodiments include the expression/overexpression of bioH, however in some cases, the pimelate methyl ester is desired. In some embodiments, expression of a thioesterase increases the production of pimelate or methyl pimelate.

LISTING OF REFERENCES

1. Mobley, D. Biosynthesis of long-chain dicarboxylic acid monomers from renewable resources. *US Department of Energy Report* (1999).
2. Picataggio, S. et al. Metabolic engineering of *Candida tropicalis* for the production of long-chain dicarboxylic acids. *Biotechnology (N Y)* 10, 894-8 (1992).
3. Watanabe, C. M. & Townsend, C. A. Initial characterization of a type I fatty acid synthase and polyketide synthase multienzyme complex N or S in the biosynthesis of aflatoxin B(1). *Chem Biol* 9, 981-8 (2002).
4. Yuan, L., Voelker, T. A. & Hawkins, D. J. Modification of the substrate specificity of an acyl-acyl carrier protein thioesterase by protein engineering. *Proc Natl Acad Sci USA* 92, 10639-43 (1995).
5. Dehesh, K., Jones, A., Knutzon, D. S. & Voelker, T. A. Production of high levels of 8:0 and 10:0 fatty acids in transgenic canola by overexpression of Ch FatB2, a thioesterase cDNA from *Cuphea hookeriana*. *Plant J* 9, 167-72 (1996).
6. Yuan, L. (Calgene, Dec. 14, 2005).
7. S Schneider, M. W., D Sanglard, B Witholt. Production of alkanedioic acids by cytochrome P450 BM-3 monooxygenase: oxidation of 16-hydroxyhexadecanoic acid to hexadecane-1,16-dioic acid. *Biocataysis and biotransformation* 17, 163-178 (1999).
8. Oliver, C. F. et al. A single mutation in cytochrome P450 BM3 changes substrate orientation in a catalytic intermediate and the regiospecificity of hydroxylation. *Biochemistry* 36, 1567-72 (1997).
9. Craft, D. L., Madduri, K. M., Eshoo, M. & Wilson, C. R. Identification and characterization of the CYP52 family of *Candida tropicalis* ATCC 20336, important for the conversion of fatty acids and alkanes to alpha,omega-dicarboxylic acids. *Appl Environ Microbiol* 69, 5983-91 (2003).
10. Seghezzi, W. et al. Identification and characterization of additional members of the cytochrome P450 multigene family CYP52 of *Candida tropicalis*. *DNA Cell Biol* 11, 767-80 (1992).
11. Imai, Y. Characterization of rabbit liver cytochrome P-450 (laurate omega-1 hydroxylase) synthesized in transformed yeast cells. *J Biochem* 103, 143-8 (1988).
12. Hardwick, J. P. Cytochrome P450 omega hydroxylase (CYP4) function in fatty acid metabolism and metabolic diseases. *Biochem Pharmacol* 75, 2263-75 (2008).
13. Lee, S. H., Stephens, J. L., Paul, K. S. & Englund, P. T. Fatty acid synthesis by elongases in trypanosomes. *Cell* 126, 691-9 (2006).
14. Erdmann, R., Veenhuis, M., Mertens, D. & Kunau, W. H. Isolation of peroxisome-deficient mutants of *Saccharomyces cerevisiae*. *Proc Natl Acad Sci USA* 86, 5419-23 (1989).
15. Scharnewski, M., Pongdontri, P., Mora, G., Hoppert, M. & Fulda, M. Mutants of *Saccharomyces cerevisiae* deficient in acyl-CoA synthetases secrete fatty acids due to interrupted fatty acid recycling. *Febs J* 275, 2765-78 (2008).
16. Kamisaka, Y. et al. Identification of genes affecting lipid content using transposon mutagenesis in *Saccharomyces cerevisiae*. *Biosci Biotechnol Biochem* 70, 646-53 (2006).
17. Sandager, L. et al. Storage lipid synthesis is non-essential in yeast. *J Biol Chem* 277, 6478-82 (2002).
18. Cryle, M. J. & Schlichting, I. Structural insights from a P450 Carrier Protein complex reveal how specificity is achieved in the P450(BioI) ACP complex. *Proc Natl Acad Sci U S A* 105, 15696-701 (2008).
19. Cryle, M. J., Matovic, N. J. & De Voss, J. J. Products of cytochrome P450(BioI) (CYP107H1)-catalyzed oxidation of fatty acids. *Org Lett* 5, 3341-4 (2003).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant cell that produces an omega-hydroxylated fatty acid or a dicarboxylic acid or both from endogenous fatty acids, wherein said cell comprises the enzymes of a Type II fatty acid biosynthesis pathway and a fatty acid omega hydroxylase; wherein one or more of said enzymes is encoded by a recombinant nucleic acid in said cell, and the fatty acid omega hydroxylase is one selected from the group consisting of P450 (3P2), P450 (PHP3), P450 BM3 (F87A), P450a1k1 (*C. tropicalis*; C12-C16); CPR (*C. tropicalis*); P450 (3P2) (chimeric enzyme; C6-C12); P450 (pHP3) (Rabbit; C6-C12); P450 (*P. oleovarans*; C8-C12); P450 BM3 (*B. megaterium*; C12-C18); CYP86A8 (*A. thaliana*; C12-C18); CYP703A1 (*Petunia x hybrid*; C12); CYP704B2 (*O. sativa* ssp *japonica*; C18); CYP4V2 (*H. sapiens*; C12-C16); CYP4B (*H. sapiens*; C7-C10); CYP4A (*H. sapiens*; C 10-C16); and CYP4F (*H. sapiens*; C16-C26); wherein the recombinant cell is genetically modified to remove a gene encoding YdiO, and the recombinant cell is a bacterial cell.

2. The recombinant cell of claim 1, wherein at least two of said enzymes are encoded by a recombinant nucleic acid in said cell.

3. The recombinant cell of claim 1, wherein said cell further comprises the enzymes of a Type I polyketide synthase (PKS) pathway and said Type I PKS enzymes are encoded by a recombinant nucleic acid in said cell.

4. The recombinant host cell of claim 1, wherein said cell further comprises the enzymes of a 2-keto acid biosynthesis pathway that includes mutated LeuA and KIVD encoded by a recombinant nucleic acid in said cell.

5. The recombinant host cell of claim 1, wherein said cell further comprises the enzymes of a biotin biosynthesis pathway, at least one enzyme of which is encoded by a recombinant nucleic acid in said cell, and said cell produces pimelic acid.

6. The recombinant cell of claim 1 that produces an alpha, omega-dicarboxylic acid by conversion of said omega-hydroxylated fatty acid with a fatty acid oxidase and aldehyde dehydrogenase enzymes.

7. The recombinant cell of claim 1, wherein the fatty acid omega hydroxylase is selected from the group consisting of P450 (3P2), P450 (PHP3), and P450 BM3 (F87A).

8. The recombinant cell of claim 1, wherein the host cell has been genetically modified to reduce β-oxidation of fatty acids.

9. The recombinant cell of claim 5, wherein the dicarboxylic acid has chain length from C3 to C26.

10. The recombinant cell of claim 1 that, relative to a wild-type cell of identical cell type, produces a dicarboxylic acid not produced by the wild-type cell.

11. The recombinant cell of claim 1 that contains the enzymes of a recombinant biotin biosynthesis pathway and a recombinant BioI gene and produces pimelic acid.

12. The recombinant cell of claim 1 that contains the enzymes of a recombinant Type I fatty acid biosynthesis pathway and a recombinant fatty acid omega hydroxylase gene and produces adipic acid.

13. The recombinant cell of claim 12 wherein the recombinant Type I fatty acid biosynthesis pathway includes HexA and HexB genes.

14. The recombinant cell of claim 1, wherein the recombinant cell is genetically modified to remove a gene encoding YdaB, YtcL, BioW, YdbM, YngJ, MmgC, AcdA, YngF, YsiB, YhaR, or FadN.

15. The recombinant cell of claim 1, wherein the bacterial cell is an *Escherichia*, *Enterobacter*, *Azotobacter*, *Erwinia*, *Bacillus*, *Pseudomonas*, *Klebsielia*, *Proteus*, *Salmonella*, *Serratia*, *Shigella*, *Rhizobia*, *Vitreoscilla*, *Synechococcus*, *Synechocystis*, or *Paracoccus* cell.

16. The recombinant cell of claim 1, wherein said cell produces a tetradecanedioc acid.

* * * * *